US008916192B2

(12) United States Patent
Andersen et al.

(10) Patent No.: US 8,916,192 B2
(45) Date of Patent: Dec. 23, 2014

(54) METHOD AND APPARATUS FOR THE PREPARATION OF CAPSULES

(75) Inventors: Peder Oscar Andersen, Oslo (NO); Robert Kopesky, Camden, ME (US); Christian Klein Larsen, Lillestrom (NO); Olav Gaserod, Steinberg (NO); David Harvey, Warren, ME (US); Sanhuang Tung, Thomaston, ME (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 13/418,797

(22) Filed: Mar. 13, 2012

(65) Prior Publication Data

US 2012/0177727 A1    Jul. 12, 2012

Related U.S. Application Data

(62) Division of application No. 12/827,697, filed on Jun. 30, 2010, now Pat. No. 8,153,037, which is a division of application No. 11/713,176, filed on Mar. 2, 2007, now Pat. No. 7,766,637.

(60) Provisional application No. 60/779,055, filed on Mar. 3, 2006, provisional application No. 60/879,138, filed on Jan. 8, 2007.

(51) Int. Cl.
| | |
|---|---|
| *A61K 9/48* | (2006.01) |
| *A23L 1/00* | (2006.01) |
| *B01J 13/04* | (2006.01) |
| *A23L 1/328* | (2006.01) |
| *A61J 3/07* | (2006.01) |

(52) U.S. Cl.
CPC .............. *A61J 3/07* (2013.01); *A61K 9/4816* (2013.01); *B01J 13/04* (2013.01); *A23L 1/3285* (2013.01)
USPC ........................................... 424/451; 426/98

(58) Field of Classification Search
CPC ..... A23L 1/3285; B01J 13/04; A61K 9/4816; A61J 3/07
See application file for complete search history.

(56) References Cited

U.S. PATENT DOCUMENTS

| | | | |
|---|---|---|---|
| 2,036,934 A | 4/1936 | Green | |
| 2,128,551 A | 8/1938 | Le Gloahec | |
| 2,379,817 A | 7/1945 | Mabbs | |
| 2,624,069 A | 1/1953 | Fischer, Jr. | |
| 2,932,061 A | 4/1960 | Jansen | 264/4 |
| 3,376,199 A | 4/1968 | Coles et al. | |
| 3,498,839 A | 3/1970 | Mehta | |
| 3,577,515 A | 5/1971 | Vandegaer | |
| 3,682,654 A | 8/1972 | Johnson | |
| 3,959,464 A | 5/1976 | De Savigny | |
| 4,140,516 A | 2/1979 | Scher | |
| 4,309,213 A | 1/1982 | Graber et al. | |
| 4,324,683 A | 4/1982 | Lim et al. | |
| 4,422,985 A | 12/1983 | Morishita et al. | |
| 4,426,337 A | 1/1984 | Suzuki et al. | |
| 4,481,157 A | 11/1984 | Morishita et al. | |
| 4,507,327 A | 3/1985 | Ueda et al. | |
| 4,690,816 A | 9/1987 | Hata et al. | |
| 4,695,466 A | 9/1987 | Morishita et al. | |
| 4,702,921 A | 10/1987 | Ueda et al. | |
| 5,015,448 A | 5/1991 | Vorlop et al. | |
| 5,330,835 A | 7/1994 | Kikuchi et al. | |
| 5,362,564 A | 11/1994 | Suzuki et al. | |
| 5,385,737 A | 1/1995 | Shigeno et al. | |
| 5,418,154 A | 5/1995 | Aebischer et al. | |
| 5,472,648 A | 12/1995 | Alisch et al. | |
| 5,478,570 A | 12/1995 | Sunohara et al. | |
| 5,502,077 A | 3/1996 | Breivik et al. | |
| 5,520,457 A | 5/1996 | Gontero | |
| 5,629,187 A | 5/1997 | Ors et al. | |
| 5,756,123 A | 5/1998 | Yamamoto et al. | |
| 5,827,493 A | 10/1998 | Ledon | |
| 5,882,680 A | 3/1999 | Suzuki et al. | |
| 5,942,266 A | 8/1999 | Okamura et al. | |

(Continued)

FOREIGN PATENT DOCUMENTS

| | | |
|---|---|---|
| DE | 3913772 | 10/1990 |
| DE | 19922537 A1 | 11/2000 |

(Continued)

OTHER PUBLICATIONS

Martinsen, A. et al., "Comparison of Different Methods for Determination of Molecular Weight and Molecular Weight Distribution of Alginates", Carbohydrate Polymers, vol. 15, Issue 2, pp. 171-193 (1991). Abstract only [online] www.sciencedirect.com.
English Language Abstract for JP 9025228, Jan. 28, 1997.
English Language Abstract for JP 61044810, Mar. 4, 1986.
"Liquid Core Hydrocolloid-Oil Capsules Produced in a Single Step", Nussinovitch, et al., Food Hydrocollolds, 1997, 11, 209, pp. 325 to 331.
P. Spiekermann, et al., (1987), "Animal Cells Encapsulated within Ca-Alginate Hollow-Spheres" Proc. 4[th]European Congress on Biotechnology; vol. 3, pp. 590-593; Elsevier Science Publishers B.V., Amsterdam, Printed in the Netherlands.

(Continued)

*Primary Examiner* — Humera Sheikh
*Assistant Examiner* — Subbalakshmi Prakash
(74) *Attorney, Agent, or Firm* — FMC Corporation

(57) ABSTRACT

An apparatus for a continuous encapsulation process is provided. The apparatus is a vibrating tubing used alone, in series, or in combination with an encapsulation apparatus, which is used alone or in series. The vibrating tubing is a flat coil, a standing spiral, or a flume. The encapsulation apparatus includes a winding having coils disposed in an aqueous gelling solution. The winding is rotatable about its longitudinal center axis. The winding has adjacently spaced coils forming a plurality of chambers. Objects to be encapsulated are added to the apparatus such that when the winding is rotated, the chambers transport a volume of objects through the length winding in the aqueous gelling solution in a predetermined time.

9 Claims, 10 Drawing Sheets

(56) References Cited

U.S. PATENT DOCUMENTS

| | | |
|---|---|---|
| 5,976,604 A | 11/1999 | Kunieda et al. |
| 6,106,815 A | 8/2000 | Kang et al. |
| 6,165,615 A | 12/2000 | Itakura et al. |
| 6,214,376 B1 | 4/2001 | Gennadios |
| 6,251,661 B1 | 6/2001 | Urabe et al. |
| 6,325,859 B1 | 12/2001 | De Roos et al. |
| 6,458,818 B1 | 10/2002 | Lipari et al. |
| 6,719,933 B2 | 4/2004 | Nakamura et al. ............. 264/14 |
| 6,982,095 B2 | 1/2006 | Asada et al. |
| 7,585,538 B2 | 9/2009 | Mangos et al. |
| 2003/0082272 A1 | 5/2003 | Bouwmeesters et al. |
| 2003/0219514 A1 | 11/2003 | Jones et al. |
| 2004/0022845 A1 | 2/2004 | Zhang |
| 2004/0191366 A1 | 9/2004 | Mangos et al. |
| 2005/0095337 A1 | 5/2005 | Kelly et al. |
| 2005/0095338 A1* | 5/2005 | Fernandes et al. ............. 426/573 |
| 2005/0106233 A1* | 5/2005 | Andersen et al. ............. 424/451 |
| 2006/0096252 A1 | 5/2006 | Nakamura et al. |
| 2007/0275163 A1 | 11/2007 | Dunaitschik |
| 2011/0287166 A1 | 11/2011 | Dunajtschik |

FOREIGN PATENT DOCUMENTS

| | | |
|---|---|---|
| EP | 0212875 | 4/1987 |
| EP | 0 470 872 A1 | 2/1992 |
| EP | 0 480 729 | 4/1992 |
| EP | 0173915 B1 | 8/1992 |
| EP | 0 513 603 | 11/1992 |
| EP | 0 655 241 | 5/1995 |
| EP | 1020177 A1 | 7/2000 |
| EP | 1025842 A1 | 8/2000 |
| EP | 1 072 259 | 1/2001 |
| EP | 1690518 | 8/2006 |
| FR | 2521428 A1 | 8/1983 |
| GB | 1163023 A | 9/1969 |
| GB | 2192171 A | 1/1988 |
| HU | 53800 | 12/1990 |
| JP | 48-16183 B | 5/1973 |
| JP | 55-7241 A | 1/1980 |
| JP | 58-88027 | 5/1983 |
| JP | 58-172313 A | 10/1983 |
| JP | 59-88420 A | 5/1984 |
| JP | 61010508 | 1/1986 |
| JP | 59166916 | 3/1986 |
| JP | 61044810 | 3/1986 |
| JP | S61-044810 | 3/1986 |
| JP | 62282772 | 5/1989 |
| JP | 01082853 | 2/1990 |
| JP | 63-265514 | 4/1990 |
| JP | 02078799 | 12/1991 |
| JP | 03280846 | 12/1991 |
| JP | 04046099 | 7/1992 |
| JP | H06-055060 | 3/1994 |
| JP | H06-079165 | 3/1994 |
| JP | 7196478 | 8/1995 |
| JP | 2519485 | 7/1996 |
| JP | 9025228 | 1/1997 |
| JP | 2589556 | 3/1997 |
| JP | 07297573 | 4/1997 |
| JP | 09-327501 A | 12/1997 |
| JP | 09-827501 | 12/1997 |
| JP | H11-113549 | 4/1999 |
| JP | 2000-325431 | 11/2000 |
| LV | 11585 | 2/1997 |
| WO | WO 89/01034 | 2/1989 |
| WO | WO-99/02252 | 1/1999 |
| WO | WO 99/18938 | 4/1999 |
| WO | WO-03030874 A1 | 4/2003 |
| WO | WO 03084516 A1 | 10/2003 |
| WO | WO-2004060356 A1 | 7/2004 |

OTHER PUBLICATIONS

Research Article "A Novel, Self correcting Membrane Coating Technique", Hitesh R. Bhagat, Pharmaceutical Research, vol. 8, No. 5, 1991, pp. 576-583.

"Cell Immobilization within Coated Alginate Beads or Hollow Fibers Formed by Ionotropic Gelation", Vorlop, et al., 1987, Enzyme Engineering, 8, pp. 339-342.

Patel, et al. (2000) "A Novel Encapsulation Technique for the Production of Artificial Seeds", Plant Cell Reports, 19, 868-874.

Olav Gaserod et al; "Microcapsules of alginate-chitosan—I A quantitative study of the interaction between alginate and chitosan"; Biomaterial: vol. 19; pp. 1815-1825; 1998.

Olav Gaserod et al; "Microcapsules of alginate-chitosan. II. A study of capsule stability and permeability"; Biomaterials; vol. 20; pp. 773-783; 1999.

International Preliminary Report on Patentability and Written Opinion Dated Sep. 9, 2008, International Application No. PCT/US2007/005387.

\* cited by examiner

METHOD AND APPARATUS FOR THE PREPARATION OF CAPSULES

CROSS-REFERENCE TO RELATED APPLICATIONS

This application claims priority of U.S. Provisional Application Ser. No. 60/779,055, filed Mar. 3, 2006, and U.S. Provisional Application Ser. No. 60/879,138, filed Jan. 8, 2007, the disclosures of which are incorporated herein by reference.

FIELD OF THE INVENTION

The invention relates to seamless capsules in which the capsule comprises a gelled gel-forming polysaccharide. More particularly, this invention relates to an apparatus for the continuous manufacture of the seamless capsules.

BACKGROUND OF THE INVENTION

The use of gelatin capsules to deliver a wide variety of agents, such as pharmaceuticals, is well known. The primary sources of gelatin are bovine animals, e.g., cows, and pigs. However, for various aesthetic, religious, and/or health-related reasons, it has become desirable to replace the gelatin in capsules with other materials that are not derived from animal sources.

A method for the preparation of seamless capsules that have a layer of gelled gel-forming polysaccharide as the capsule wall has been described in United States Published Patent Application 2005/0106233, the disclosure of which is incorporated herein by reference. In this method, the capsules are made by a method involving the steps of: (a) preparing an emulsion comprising oil, water, emulsifier, gelling agent, and optional added component; and (b) adding portions of the emulsion to an aqueous gelling solution comprising a gel-forming polysaccharide, thereby encapsulating the portions of the emulsion in a layer of gelled gel-forming polysaccharide, and optionally (c) drying the resulting capsules by removing water. Although this method provides significant advantages for the preparation of non-gelatin-containing seamless capsules, a need exists for an apparatus capable of carrying out this method as a continuous process.

SUMMARY OF THE INVENTION

In one aspect, the invention is an apparatus and method for the continuous encapsulation of objects, such as portions of an emulsion comprising oil, water, emulsifier, gelling agent, and optional added component, with a layer of gelled gel-forming polymer using an encapsulation apparatus. The apparatus has a cylindrical drum having a length, an input end, and an output end. Disposed in the drum is a winding comprising coils. The winding is rotatable about a longitudinal center axis of the drum. The winding may be in the form of a helical screw, an inverted screw or in the form of a (regular) conveyor screw. The coils of the winding and the interior surface of the drum form a plurality of chambers. The winding is rotated by means of any conventional drive systems capable of rotating the winding in a controlled and accurate manner.

Objects to be encapsulated, such as portions of the emulsion described below, are added at the input end of the drum to a first chamber of the winding either through an addition device, such as a flume, or directly into the drum itself. The drum has a volume of gelling solution contained within each chamber or added to the first chamber concurrently with the addition of the objects to be encapsulated. The objects to be encapsulated are conveyed through the winding in a predetermined time (controlled by the rotation, pitch, size and number of coils in the winding). Baffles are added for introduction of proper agitation during the encapsulation process. The encapsulated objects, or capsules, are discharged at the output end of the drum.

In another aspect, the invention is an apparatus for continuous capsule formation comprising a tray for containing a volume of gelling solution. The tray has a front and a rear wall, side walls that are longer than the front and rear walls, and a bottom. A support plate is disposed in the tray. Also disposed within the tray is a winding comprising coils. The winding is disposed on top of the plate such that the coils of the winding and the plate form a series of chambers, which are immersed in the gelling bath. When an object to be encapsulated is placed into the apparatus, the object is submerged in the gelling bath and is moved through the apparatus by the rotation of the winding in a predetermined time. The rotation of the winding also imparts a turbulent flow to the gelling bath.

According to an exemplary embodiment of the invention, the apparatus includes a cylindrical drum having a length, an input end, and an output end. Disposed in the drum is a winding comprising coils. The winding is rotatable about a longitudinal center axis of the drum. The winding forms a plurality of chambers having sides defined by adjacent coils of the winding and a floor defined by an interior surface of the drum. The rotation of the winding transports a volume of material added to a chamber from the drum input end through the length of the drum to the drum output end in a predetermined time. In a further exemplary embodiment, the apparatus has a beach affixed to the front of the drum whereby material is added through the beach.

One exemplary use of the apparatus is for liquid processes in which objects require lengthened reaction time in a liquid, e.g., for a process where capsules are gelled in a gelling solution. It is possible to control the residence time of the processed material accurately, within the desired specific boundary for residence time.

Another exemplary use of an exemplary embodiment of an apparatus of the invention has a screw having a length, an input end, and an output end. The screw has coils and is disposed in a drum. The screw is rotatable about a longitudinal center axis of the screw and it has a plurality of baffles disposed on the coils at oblique angles to the longitudinal axis of the screw. The screw forms a plurality of chambers having sides defined by adjacent coils of the screw and a floor defined by a surface of the drum. The use of the apparatus to encapsulate objects includes the steps of:

(a) providing an emulsion comprising oil, water, an emulsifier, and a gelling agent in which the oil is present in an amount of at least 50% by weight of said emulsion;

(b) continuously adding the emulsion at the drum input end into a chamber comprising an aqueous gelling solution;

(c) rotating the screw to transport the portion of the emulsion in the chamber containing the aqueous gelling solution through the length of the drum to the drum output end in a predetermined time;

(d) agitating the emulsion and aqueous gelling solution during transport through the drum via the baffles disposed on the screw coils; and (e) forming a capsule wall encapsulating the emulsion, in which the gelling agent gels the gel-forming polymer to form a gelled gel-forming polymer, and in which the capsule wall comprises the gelled gel-forming polymer.

A further embodiment of the invention comprises encapsulation of objects by continuously adding material to a liquid stream that is flowing in an outer constraint and being vibrated. The outer constraint may be in the form of a hose, flume, tube, U-shaped tube, U-shaped tube with additional lid, channel, or canal, and may be either a straight flume, a flat coiled, or formed into a standing spiral. Adding vibration to the continuous liquid stream makes it possible to have high throughputs of encapsulated material in a relatively small volume, and makes it possible to also encapsulate objects that are sticky during encapsulation. Adding vibration to the continuous liquid stream also makes it possible to encapsulate and gel material in the liquid stream with significantly lower residence time variation than in a non-vibrating system. This exemplary embodiment is referred to herein as a vibrating tubing.

The device responsible for imparting the vibration to the tubing may be a shaking table, vibrating table, vibrating screen or an attached vibrating element, which provides proper agitation such that sticking is avoided and such that encapsulated material is not deteriorated.

A closed system, such as a spiral-shaped tubing placed on top of a vibrating screen, such as a SWECO® screen, may be of particular advantage in order to reduce liquid spillage during operation. A closed system such as an U-shaped tube with removable lid may also be advantageous as this system is also closed but may be easily opened for cleaning if needed.

Yet another exemplary use of the apparatus is for the manufacture of polysaccharide beads, e.g., alginate beads. The process includes introducing a polysaccharide solution, e.g., an alginate solution, into a gelling solution comprising a gelling ion such as, i.e., calcium ion ($Ca^{2+}$).

According to still a further aspect of the invention, the objects may be encapsulated by passing them through the encapsulation device, the vibrating tubing, or the encapsulation device in combination with the vibrating tubing.

BRIEF DESCRIPTION OF THE DRAWINGS

The invention may be understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Unless the context indicates otherwise, in the specification and claims, the terms gel-forming polysaccharide, gel-forming polymer, oil, emulsifier, gelling agent, added component, and similar terms also include mixtures of such materials. Unless otherwise specified, all percentages are percentages by weight and all temperatures are in degrees Centigrade (degrees Celsius). Ambient temperature means a temperature of about 20° C. to about 30° C.

As disclosed in United States Published Patent Application 2005/0106233, the disclosure of which is incorporated herein by reference, seamless capsules are prepared by a process comprising the steps of: (a) preparing an emulsion comprising oil, water, emulsifier, gelling agent, and optional added component, and (b) adding portions of the emulsion to an aqueous gelling solution comprising of a gel-forming polymer (gel-forming polysaccharide), thereby encapsulating the portions of the emulsion in a layer of gelled gel-forming polymer (gelled gel-forming polysaccharide), and optionally (c) drying the resulting capsules by removing water. The apparatus described herein is capable of carrying out this method, and other methods, in a continuous manner. Although some aspects of the apparatus may be described with respect to this method, the apparatus and its use are not limited to this method.

Apparatus

Figure 1:
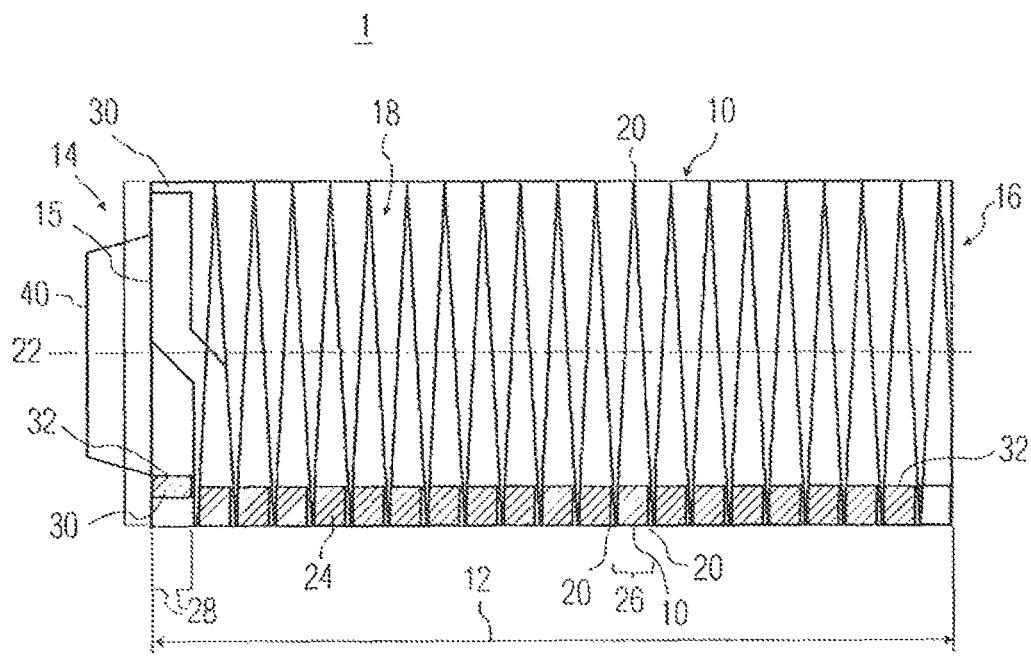
FIG. 1 is a cut-away side view of an exemplary embodiment of the encapsulation apparatus of the invention.

FIG. 1 is a cut-away side view of an exemplary embodiment of the encapsulation apparatus. Encapsulation apparatus 1 includes drum 10 defined by a length 12 and having input end 14 with a front plate 15 and a beach 40 and output end 16. Disposed in drum 10 is winding 18 comprised of a series of contiguous coils 20. In the exemplary embodiment shown in FIG. 1, 20 coils comprise winding 18. Winding 18 may have a hollow core, or be entirely solid (e.g., having the appearance of an agar drill bit). Winding 18 rotates freely within drum 10 about center axis 22 or is fixedly attached to drum 10 by smooth welds, such that drum 10 and winding rotate together about center axis 22. It is possible to add several windings in series, by either combining windings closely together or by discharging one winding into a flume and feeding the new winding with this flume. If two or more windings are in series it may not be necessary to impart a declining floor in all windings (discussed in more detail below).

Encapsulation apparatus 1 is oriented so that drum length 12 is perpendicular to the pull of gravity. A gelling solution 24, such as is described below, is added into encapsulation apparatus or is maintained within encapsulation apparatus 1. As a result, adjacent coils 20 together with drum 10 to form a plurality of chambers 26 along the length of winding 18 filled with gelling solution 24. When winding 18 is rotated and an added volume of material is placed into chamber 26, the added material in chamber 26 is transported through the length 12 of drum 10 in a predetermined amount of time, referred to as the residence time.

Emulsion fragments to be encapsulated may generated by, for example, dropping the emulsion from a pipette, a single or multiple nozzle, or a vibrating nozzle; extruding the emulsion through a chopping mechanism such as a metal or plastic wire such as a nylon or TEFLON® resin coated wire; or molding the emulsion in a casting mold. As described below, the emulsion fragments may be, for example, portions of an emulsion comprising oil, water, emulsifier, gelling agent, and, optionally, added component.

Figure 11:
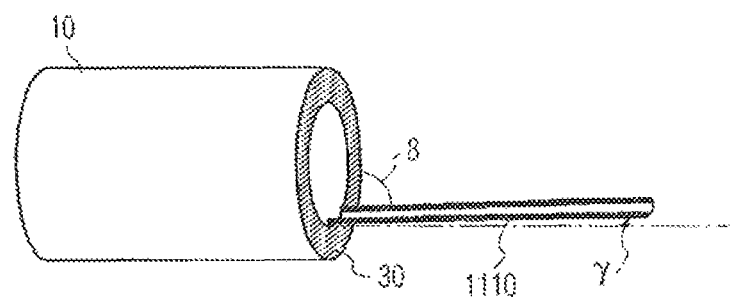
FIG. 11 is a is a side view an input end of a drum of an exemplary embodiment according to the encapsulation apparatus of the invention.

Objects to be encapsulated, such as the emulsion fragments, are introduced into encapsulation apparatus 1 at input end 14 directly or with the assistance of the following embodiments. According to one embodiment, the objects are added to encapsulation apparatus 1 by means of flume 1110, shown in more detail in FIG. 11. Flume 1110 may be disposed parallel to drum 10 or at a slight inclination to drum 10 such that capsule fragments do not adhere to each other as they travel down flume 1110. Angle δ represents the angle in the horizontal plane between flume 1110 and the horizontal screw rotation axis. Angle γ represents the angle in the vertical plane (slope) between flume 1110 and the horizontal screw rotation axis. The angle of flume 1110 is such the objects are not damaged on addition to the gelling solution.

According to another embodiment, the objects are added to the encapsulation apparatus 1 by means of a vibrating tubing. Exemplary embodiments of a vibrating tubing include a flat coil, a standing spiral, and a flume, as shown and described in more detail with respect to FIGS. 16-20. In each of these embodiments, the configuration of the vibrating tubing input end is such that the vibration of the coil allows gelling solution and capsule fragments to flow continuously therethrough in such a manner that the capsule fragments do not adhere to each other as they flow from fragment formation to the encapsulation apparatus 1. The angle of discharge of the capsules from the vibrating tubing is such that objects to be encapsulated are not damaged by their passing from the vibrating tubing to encapsulation apparatus 1. The objects to be encapsulated may additionally enter the vibrating tubing through the flume shown in FIG. 21.

According to another embodiment, objects are added to encapsulation apparatus 1 by way of beach 40. Beach 40 is a flat or slightly angled surface which receives objects directly or receives objects from flume 1110. Beach 40 serves to gradually guide objects into the first chamber. Beach 40 may be directly secured to front plate 15 of drum 10. When using beach 40, the gelling solution height in the first chamber may be lower or higher than the gelling solution height at the junction of beach 40 and front plate 15. The angled surfaces of beach 40 maintain the height of the gelling solution substantially constant and help prevent objects from being damaged as they travel into first chamber 28.

Figure 21:
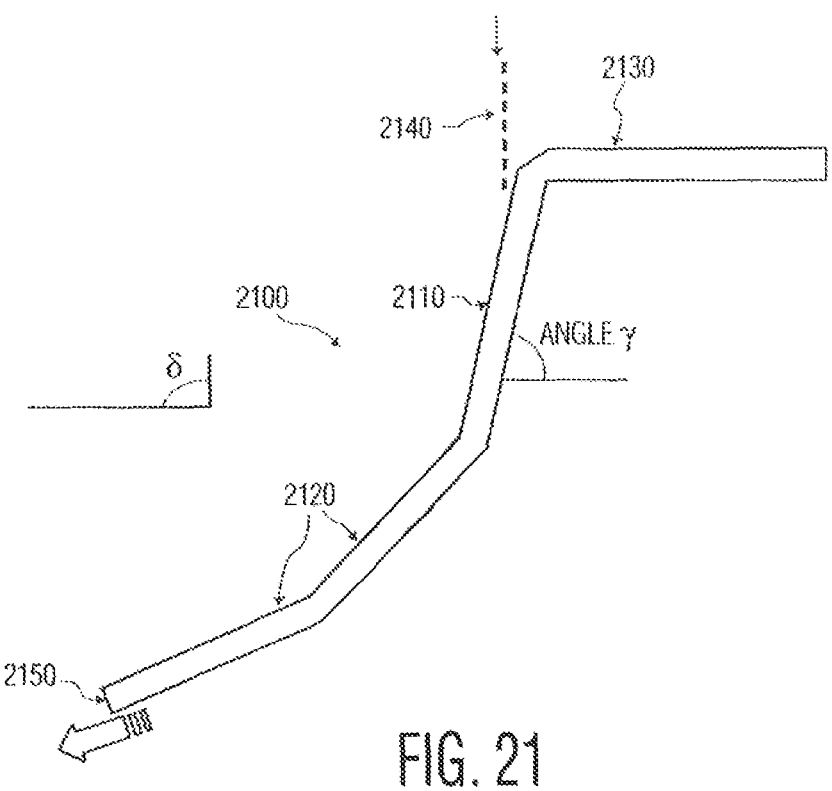
FIG. 21 is a side view of a flume with varying flume angles, in which the initial part of the flume is steeper than the latter part.

According to a further embodiment, flume 1110, the flume shown in FIG. 21, or a vibrating tubing, may be used in conjunction with beach 40. Beach 40 may be a unibody construction with front plate 15 and constructed such that when beach 40 is at a slight angle and unibody with front plate, objects can slide down beach 40 and be directly incorporated into the first coil of the winding through rotation of the winding. Beach 40 is affixed to encapsulation apparatus 1, either via front plate or by other means, in such a manner that acute angles between winding 18 or any part of front plate 15 have been minimized or eliminated such that processed material is not entrapped in an unwanted manner.

According to a further embodiment, the output of the vibrating tubing may be used in conjunction with beach 40. Beach 40 may be a unibody construction with front plate 15 and constructed such that when beach 40 is at a slight angle and unibody with front plate, objects can slide down beach 40 and be directly incorporated into the first coil of the winding 18 through rotation of the winding. Beach 40 is affixed to encapsulation apparatus 1, either via front plate or by other means, in such a manner that acute angles between winding 18 or any part of front plate 15 have been minimized or eliminated such that processed material is not entrapped in an unwanted manner.

Objects to be encapsulated are added as separate objects into the gelling solution. As the objects are added either directly into the first chamber 28 (defined by winding 18, the floor of drum 10, and front plate 15 of drum 10) or first disposed on beach 40, the height of gelling solution 24 disposed in first chamber 28 is maintained at a substantially constant height as first chamber is rotated by declining floor 30.

Referring again to FIG. 1, as the objects are added to the first chamber 28 (defined by winding 18, the floor of drum 10, and front plate 15 of drum 10), the height of gelling solution 24 disposed in first chamber 28 is maintained at a generally constant height as first chamber 28 is rotated. This helps to ensure that no distortion of the objects occur as they are added into the first chamber. According to the embodiment using beach 40, the volume created by the angled surface of the beach with the first chamber serves to minimize the change in the height of the gelling solution as objects are added and first chamber 28 is rotated.

The degree to which the objects are agitated in the first chamber 28 is dependent on the height of the gelling solution in the first chamber and the height of baffles 310 in the first chamber. The height of the gelling solution in the first chamber is maintained generally constant so that the emulsion fragments are not distorted and do not adhere to each other. According to one exemplary embodiment, to maintain the height of the gelling solution in the first chamber as emulsion fragments are added and the first chamber is rotated, the first chamber 28 is fitted with a declining floor, or the first and second coils that define the first chamber may be varied in width such that the volume of the first chamber 28 is varied.

Figure 2:
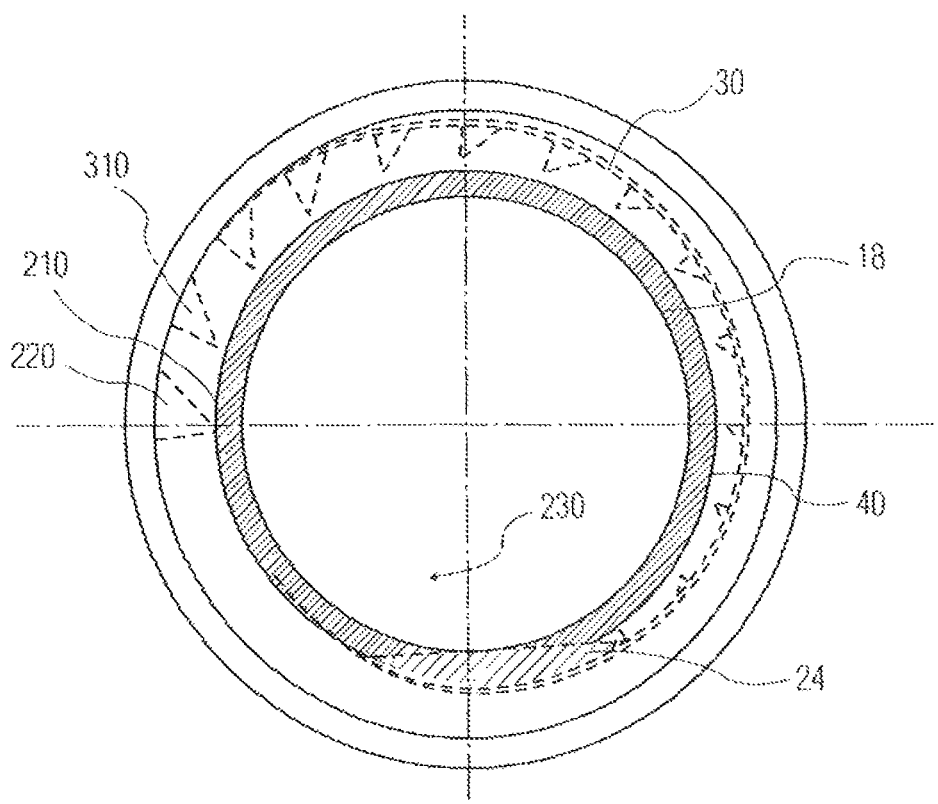
FIG. 2 is a front view of the encapsulation apparatus of FIG. 1.

Declining floor 30 is discussed in more detail in FIG. 2. Gelling solution 24 and the objects to be encapsulated are then moved from first chamber 28 by means of angled diverter plate 22 into chamber 26. As drum 10 or winding 18 rotates, the objects are encapsulated while they travel through the length of drum 10 to the drum output end 16. The resulting capsules and gelling solution 24 are discharged at output end 16 of drum 10. The capsules may then be isolated from the liquid by a separation technique such as sifting.

Gelling solution 24 may then be either disposed of or recycled back into the process. After separation the capsules can be washed and dried, or added into a new process step, such as a washing step or an additional plasticizing step.

Referring again to the embodiment shown in FIG. 1, first chamber 28 is parallel to front plate 15. This enables the gelling solution height in first chamber 28 to be more constant throughout the rotation of winding 18 and filling of drum 10 with objects to be encapsulated. With this exemplary embodiment of first chamber 28, shown in detail in FIG. 11, the output of flume 1110 is closer to the gelling solution thereby minimizing stress of the objects traveling from flume 1110 into the gelling solution 24 disposed in first chamber 28. In order for the objects to pass into the subsequent chambers 26 from first chamber 28, an angled diverter plate 34 is added.

Figure 12:
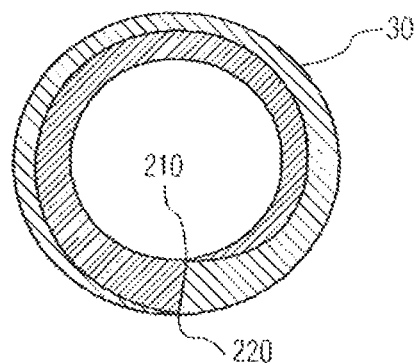
FIG. 12 is a front view of a first chamber of an exemplary embodiment of the winding according to the encapsulation apparatus of the invention.

FIG. 2 is a front view of the encapsulation apparatus of FIG. 1, also shown in more detail of FIG. 12. In this exemplary embodiment, disposed in first chamber 28 is declining floor 30. Declining floor 30 has a first height 210 and a second height 220 disposed substantially at the same point on first chamber 29 near angled diverter plate 22 (not shown in FIG. 2). First height 210 is not as tall as winding 18, thus objects and gelling solution are prevented from spilling into other chambers during agitation. Declining floor 30 declines in height until declining floor 30 is at the same height as the floor of drum 10. Also shown in the exemplary embodiment of FIG. 2 is the beach 40 attached to the front plate 15. Beach 40 is attached to the front plate 15 at a height similar to the upper position of the incremental baffles 310. Also shown in the exemplary embodiment of FIG. 2 are baffles 310 that increase in height as declining floor 30 decreases. First chamber 28 rotates in the direction of arrow 230. In this manner, as winding 18 or drum 10 rotates and the objects and gelling solution 24 are added to first chamber 28, the objects and gelling solution 24 are agitated as they pass over the incremental baffles 310 and the height of declining floor 30 declines such that the height of gelling solution 24 is maintained constant throughout a rotation of first chamber 28.

Figure 3:
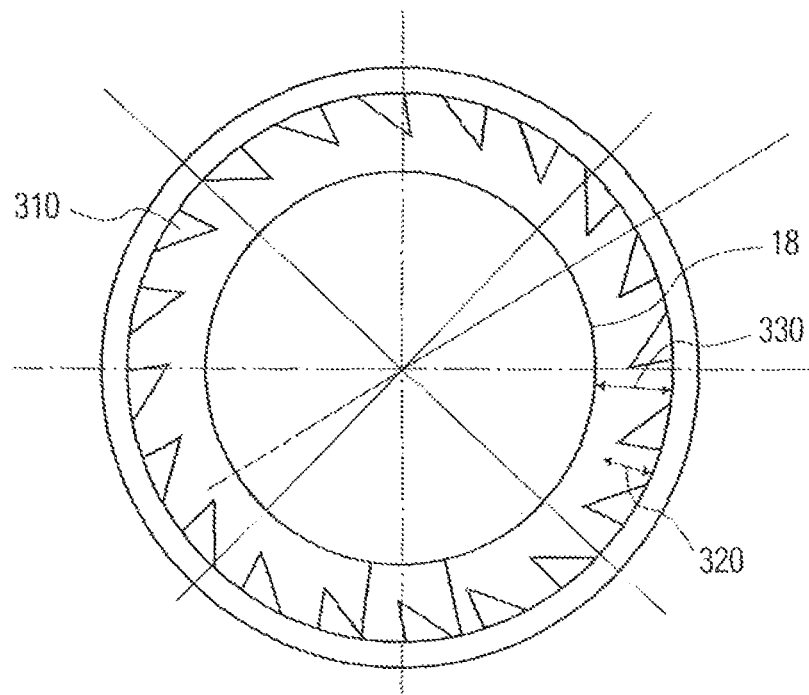
FIG. 3 is a rear view of the encapsulation apparatus of FIG. 1.

FIG. 3 is a rear view of the encapsulation apparatus of FIG. 1. FIG. 3 shows a plurality of angled baffles 310 disposed adjacent winding 18. The height and design of baffles 310 must not be such that the liquid and gelled objects are lifted from one chamber into another chamber, i.e., for baffle designs similar to the exemplary embodiments illustrated in FIGS. 2-4, 7, and 10, height 320 of baffle 310 must be lower than the height 330 of winding 18. The rotation rate and the dimensions, shape and number of baffles 310 disposed between adjacent coils of winding 18 should provide sufficient agitation within an individual chamber to prevent objects from adhering to each other or to baffles 310, coils 20, and winding 18. However, the agitation from baffles 310 and the rotation of the encapsulation apparatus should not produce such a high agitation that deterioration and breakage of the objects undergoing encapsulation occurs.

Figure 4:
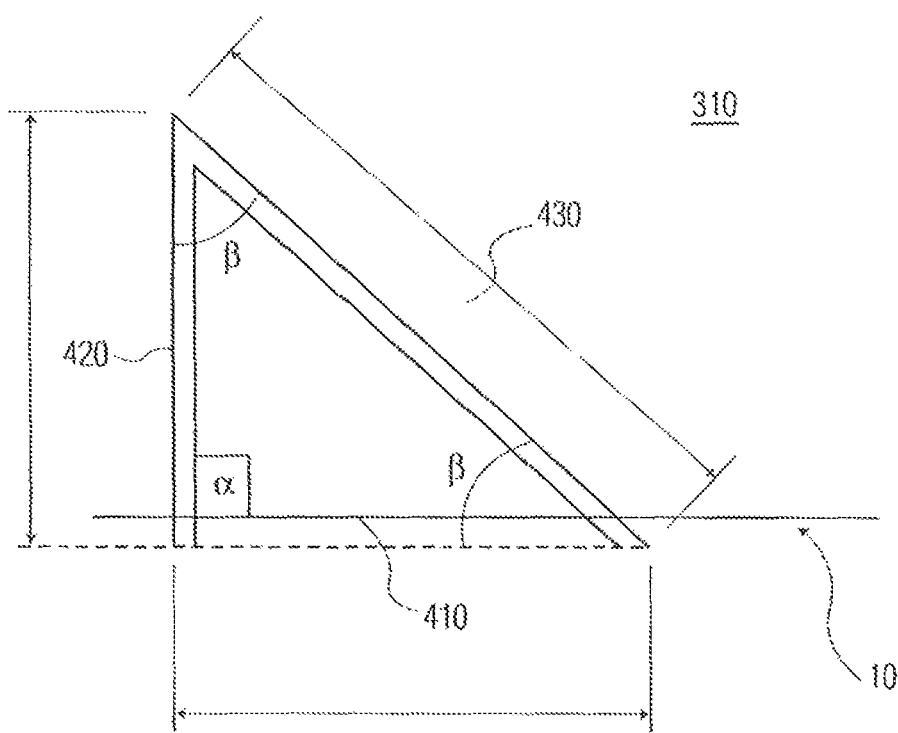
FIG. 4 is a detailed view of an exemplary baffle of the encapsulation apparatus of FIG. 3.
Figure 7:
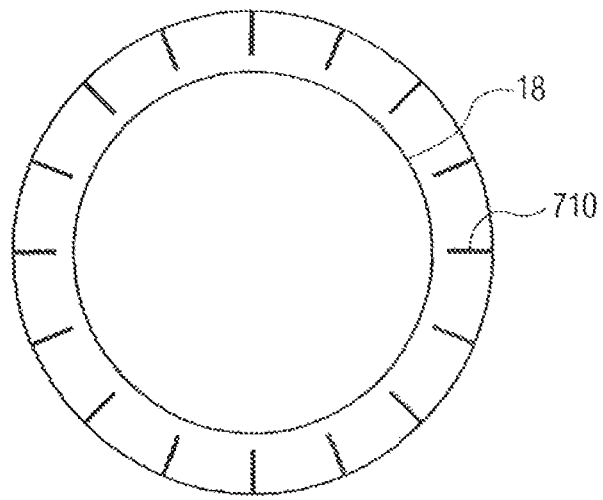
FIG. 7 is an end view of an alternative embodiment of the baffle arrangement according to an encapsulation apparatus of the invention.

FIG. 4 is a detailed view of an exemplary baffle 310 of the encapsulation apparatus of FIG. 3. The shape of baffle 310 may have the form of a plate, angled plate, triangle, rod, or any other suitable shape as would be understood by one skilled in the art. Baffle 310, shown in FIG. 4, has the general shape of a triangle. Baffle 310 has a height 410, base 420, and angled side 430. The exemplary embodiment of baffle 310 shown in FIG. 4 forms a right triangle, having an angle α of 90° and two 45° angles β. Base 410 of baffle 310 may be secured to the interior surface of the drum 10, or alternatively, the sides of the baffle may be secured to adjacent coils 20, so that winding 18 may be rotated and drum 10 may remain stationary. FIG. 7 illustrates another exemplary embodiment of a side view of drum 10 with baffles 710 having a height that is less than the height of winding 18. According to the exemplary embodiment shown in FIG. 7, baffles 710 are attached to every other winding.

Figure 8:
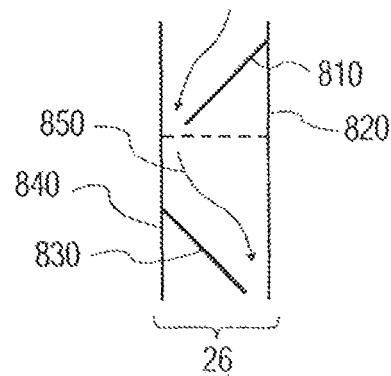
FIG. 8 is a schematic of an exemplary embodiment of the arrangement of the baffles according to an encapsulation apparatus of the invention.

FIG. 8 is a top view of a portion of an exemplary embodiment of a chamber 26 according to the invention. According to the embodiment in FIG. 8, baffle 810 is a plate attached to and forming an angle β with coil 820. Another baffle 830 is disposed downstream of and attached to an adjacent coil 840, also forming an angle β with coil 840. The arrangement of the baffles according to the embodiment shown in FIG. 8 imparts turbulent flow as shown by arrows 850. Baffles 810 and 830 are shown as attached to every other winding forming a gap which allows material to pass around each baffle, but may also be added to the same winding. In this configuration, the baffles may be of similar or higher height than the winding 18 itself, as the gap ensures that no material is moved from one coil to a neighboring coil by passing over the coil. Alternatively, two (2) or more baffles may be disposed on consecutive windings or a baffle may span the distance from one coil to the adjacent coil, forcing the gelling solution and objects to pass over the baffle as the winding is rotated. In this configuration the baffle has a height that is less than the height of the adjacent coils such that gelling solution and object do not spill over the coil.

Figure 9:
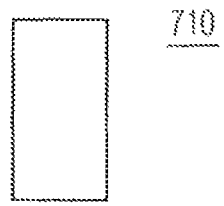
FIG. 9 is an exemplary embodiment of a baffle according to an encapsulation apparatus of the invention.

FIG. 9 shows a plan view of baffle plate 710 shown in FIG. 7.

Figure 10:
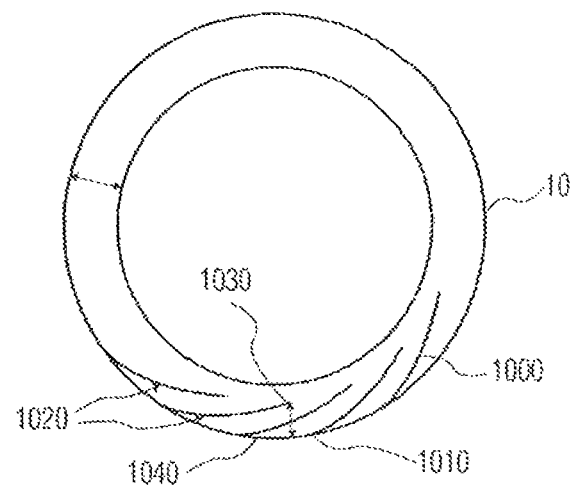
FIG. 10 is an end view of an alternative embodiment of the baffle arrangement according to an encapsulation apparatus of the invention.

FIG. 10 is an end view of yet a further embodiment of the baffle arrangement according to an encapsulation apparatus of the invention. Baffles 1000 are curved plates forming an angle with the floor of drum 10. According to one embodiment, baffles 1000 may have an open side 1020 or may have a closed side 1010 to prevent materials from collecting behind baffle 1000. Baffles 1000 are shown having a length such that the end 1030 of one baffle overlaps with the beginning 1040 of the next subsequent baffle in the flow path.

Figure 5:
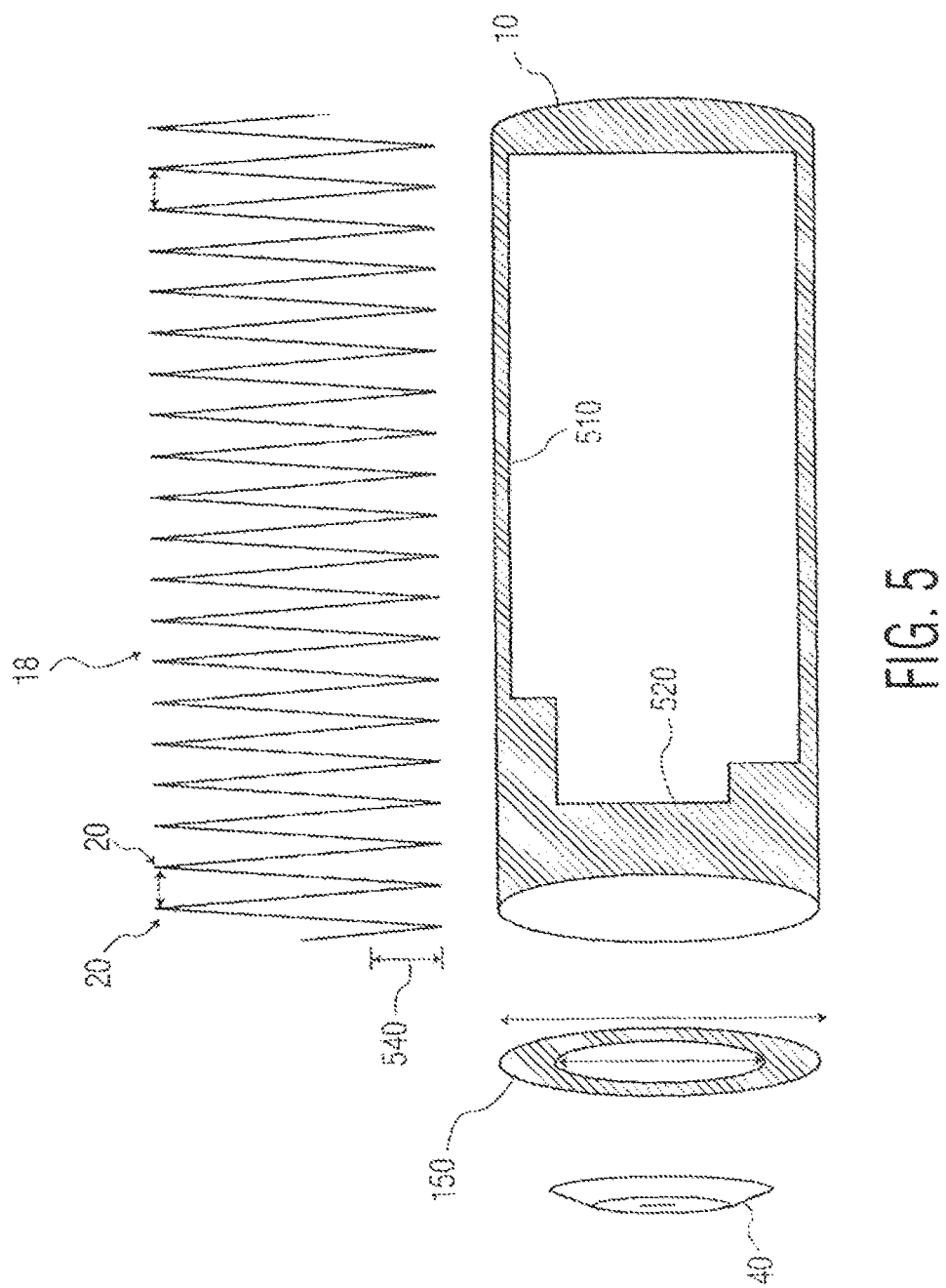
FIG. 5 is an exploded view of an exemplary winding and drum according to an encapsulation apparatus of the invention.

Referring now to FIG. 5, which is an exploded view of an exemplary winding 18 and drum 10, front plate 15, and beach 40 according to an exemplary embodiment of the invention, drum 10 has a length 510 and a height 520. The length 510 of drum 10, the height 520 of drum 10, the width of the chambers 530, and the height 540 of coils 20, together with the size and number of baffles 310 (not shown in FIG. 5) determines the maximum working volume of each chamber 26. According to this embodiment of the invention, winding 18 is prolonged and attached to the front plate without adjustments in the form of a first compartment 28 described in relation to FIG. 1. Beach 40 provides a means of adding objects and gelling solution into the drum without passing just above the first coil of the winding as the winding is rotated. Objects can be added directly to the beach 40 or to the beach via a flume. This exemplary configuration provides another means for keeping the liquid level in the first rotation relatively constant, and minimizes the stress exerted on the objects to be encapsulated. A declining floor may in this case be optional. The winding may advantageously be slightly modified in order to be attached to front plate 15 or beach 40 in such way that there are no acute angles between winding or any part of the front plate, beach outer rim, as such angles may entrap processed material in an unwanted manner. The height of the front plate may be adjusted, in which case the beach is attached straight to the outer rim, up to a height similar to the height of the winding. The upper height of the beach may advantageously be higher than the height of the windings, giving an opportunity to wash the drum by using an amount of cleaning solution, such as hot water, that would completely cover the winding, and still would be retained within the drum by the height of the beach.

Figure 6:
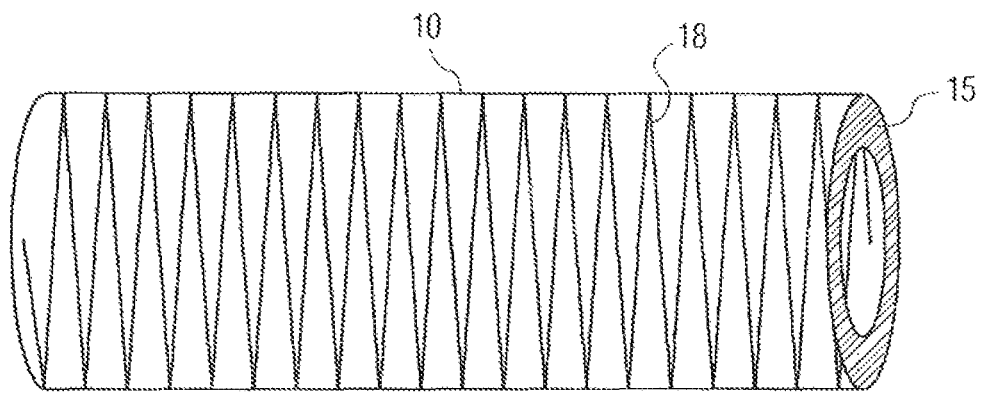
FIG. 6 is a schematic view of the winding and drum of FIG. 5.

FIG. 6 illustrates winding 18 housed in or disposed in drum 10 with front plate 15. In addition, the height 540 of each coil 20 of winding 18 should be of a sufficient height or configured to prevent the gelling objects and gelling solution 24 from passing from one chamber to another. The rotational speed (rpm) of drum 10 or winding 18 inside a stationary drum 10, determines the total average residence time, the filling time for one chamber and amount of turbulence created during operation of the encapsulation apparatus of the invention. Therefore, the obtained residence times in the drum will be within the average residence time±½ filling time.

The material of winding 18 and the interior of drum 10 should have a surface that avoids gelling solution or gelled objects from adhering to winding 18, and the interior of drum 10. Possible materials may be electro polished or coated (e.g., with a non-stick surface agent such as a TEFLON® fluorocarbon resin) stainless steel, or a plastic, e.g., polyethylene, polypropylene or other suitable plastics as would be known by one of ordinary skill in the art.

Figure 13:
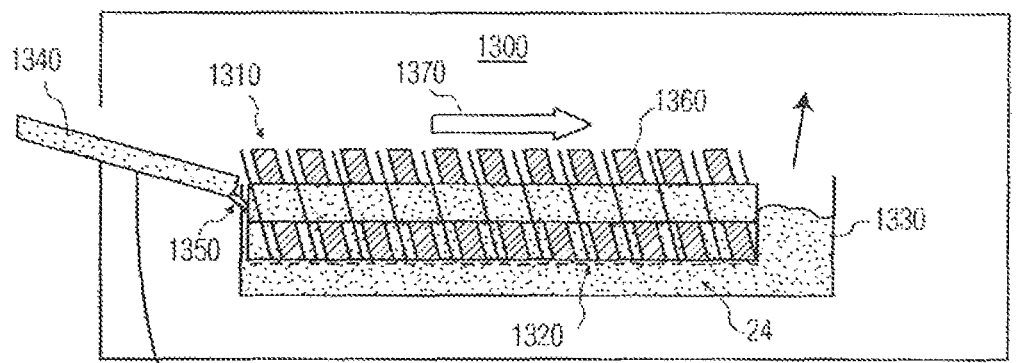
FIG. 13 is a schematic of an alternative embodiment of the encapsulation apparatus of the invention.
Figure 14:
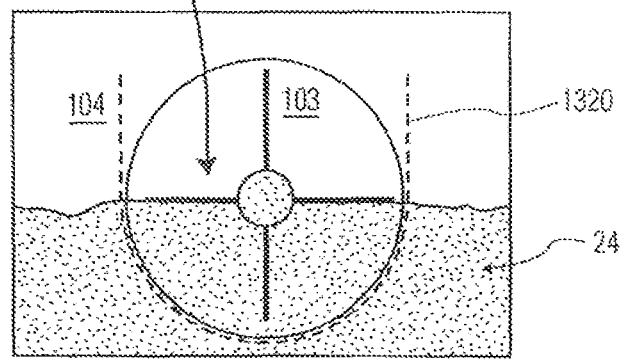
FIG. 14 is an end view of the embodiment of the encapsulation apparatus of FIG. 13.

FIG. 13 is a schematic of an alternative embodiment of the encapsulation apparatus of the invention. Encapsulation apparatus 1300 includes a winding 1310 dispose on a plate, such as perforated plate 1320. Winding 1310 and perforated plate 1320 are set into tray 1330 containing gelling solution 24. Objects to be encapsulated are fed by flume 1340, impinge upon diverter 1350 into a first chamber of winding 1310, which is submerged in gelling solution 24. The objects to be encapsulated either float in the gelling solution or sink to the bottom of the gelling solution, where they rest upon perforated plate 1320. Winding 1310 transports the objects to be encapsulated through the gelling solution in the direction of arrow 1370, where the objects to be encapsulated are exposed to the gelling solution for a predetermined residence time. The objects to be encapsulated are agitated by one or more baffles 1360. FIG. 14 is an end view of the embodiment of the encapsulation apparatus of FIG. 13.

Figure 15:
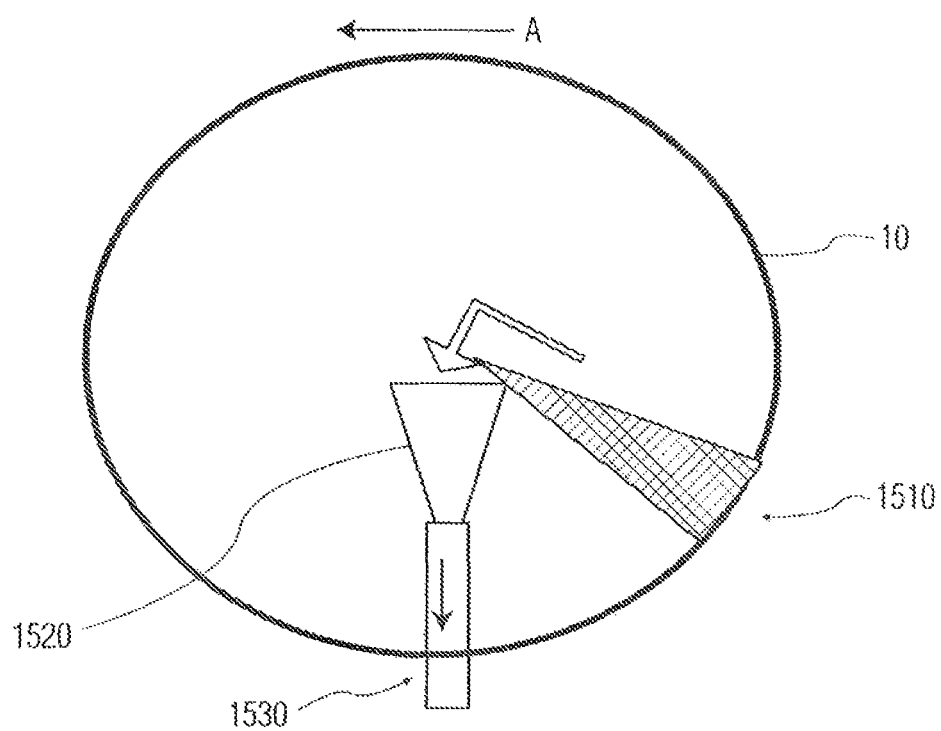
FIG. 15 is an end view of an exemplary embodiment of the output end of the drum having an elevated discharge configuration.

FIG. 15 illustrates an exemplary embodiment a lifting discharge mechanism of the output end of encapsulation apparatus 1. FIG. 15 is a side view from the output end of drum 10. Attached to the output end, in fluid communication with the last winding 19 of drum 10, is a lifting discharge mechanism comprising shaped sieve 1510. As drum 10 rotates in the direction of arrow A, encapsulated objects are transported from the last winding of the drum into shaped sieve 1510. Shaped sieve 1510 collects the encapsulated objects and guides them into a funnel 1520 or similar catching device. From funnel 1520, the capsules are transported to a drying station or rack via flume 1530. Alternatively, the shaped sieve 1510 is shaped such that the capsules may be discharged straight into further equipment, thus avoiding the use of the funnel 1520.

As discussed above, encapsulation apparatus 1 may be used in series (i.e., multiple drums) and in conjunction with a vibrating tubing, or the vibrating tubing may be use alone, or in series, depending on the desired residence time to produce the desired capsule or gelled bead to be formed.

Figure 16:
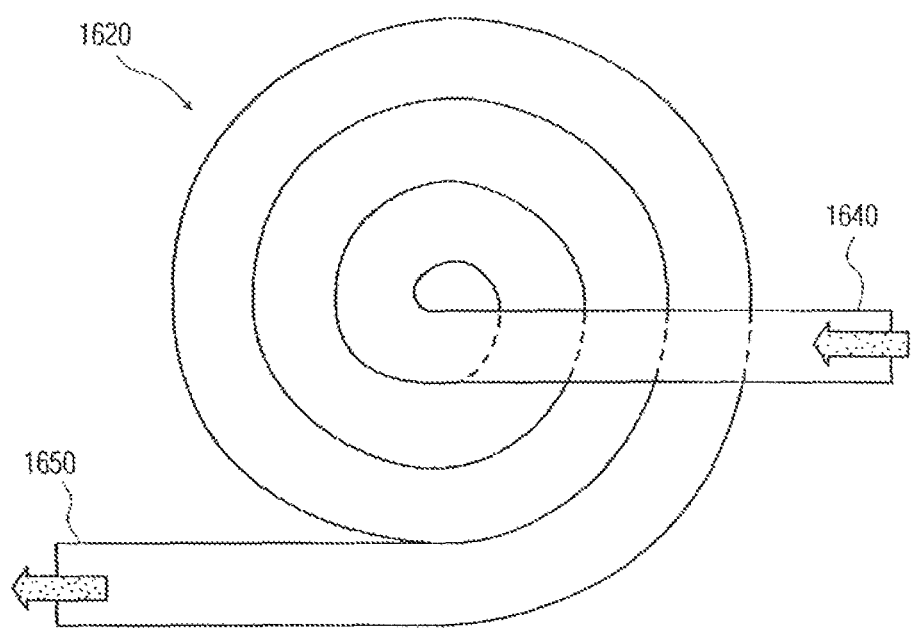
FIG. 16 is a top view of a flat coil configuration of an exemplary embodiment of a vibrating tubing.
Figure 17:
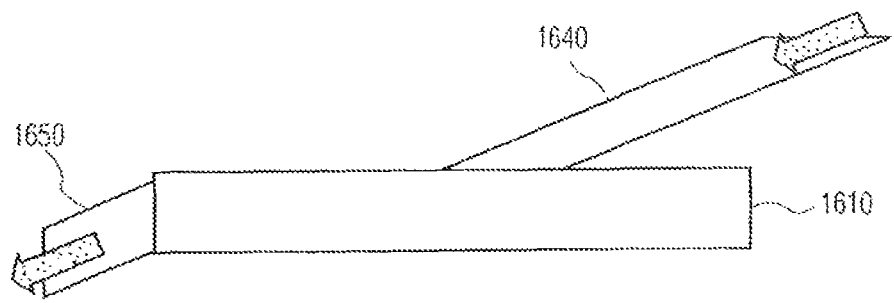
FIG. 17 is a side view of the flat coil configuration of the vibrating tubing exemplary embodiment shown in FIG. 16.

According to one exemplary embodiment of the vibrating tubing, the vibrating tubing is configured in the form of a flat coil, illustrated in FIGS. 16 and 17.

FIG. 16 is a top view of an exemplary flat coil embodiment of the vibrating tubing. According to this embodiment, the flat coil comprises a continuous spiral 1620 where the objects to be encapsulated and gelled enter at input 1640, travel through the coil, and exit at output 1650. The flat coil contains gelling solution 24. The configuration of the flat coil allows the vibrated gelling solution and capsule fragments to flow continuously therethrough in such a manner that the capsule fragments do not adhere to each other as they flow from fragment formation to output 1650. As shown in FIG. 17, the angle of the input 1640 to the spirals of the flat coil is such that objects to be encapsulated are not damaged upon entry, and the angle of output 1650 is such that the partially or completely encapsulated objects are not damaged by their passing from the flat coil to another flat coil or to an encapsulation apparatus 1 or to a further processing step such as washing or plasticizing or storage.

The flat coil embodiment of the vibrating tubing comprises continuous spiral 1620 has any desired linear length according to the thickness of the resulting encapsulation wall desired. According to one embodiment, the spiral has a linear length of approximately 1 to several hundred ft, for example 14 ft (about 4.3 M) or 35 ft (about 10.7 M). The flow within coil the can be adjusted between 0.1 and 2 ft/sec (about 0.03 to about 0.61 M/sec), for example around 0.5 ft/sec (about 0.15 m/sec). The average residence time of objects in the flat coil embodiment of the vibrating tubing depends upon the linear length of the spiral and can range from about 2 sec to at least 1200 sec, for example, 20±5 sec or 75±15 sec., upon the flow rate which is determined by the filling rate of the tubing, upon the vibrating action of the flat coil, and upon the density of encapsulated or gelled objects.

The total linear length of the vibrating tubing may be adjusted to fit the needed gelling time of the system. The linear length may be adjusted by increasing the number of coils, e.g., in the flat coil embodiment of the vibrating tubing. According to one exemplary embodiment, a series of flat coils is stacked one on top of the other to provide longer residence times if needed. In such a setup, the flat coils may be connected through a simple connection such as a pipe or a hose. Alternatively, the coils may be connected directly if the coils are winded up and in opposite directions, such that if the inlet of the lower flat coil is in the center, the outlet of the above coil is in the center. This setup with stacked, flat coils may advantageously be made with a tubing having a shape of an open U-shaped tube. With this U-shaped tubing, the flat coil stacked on top can function as a lid for the flat coil immediately below it, thus making a closed system that may be easily detached for proper washing and rinsing in cleaning procedures.

The flat coil is vibrated and may be coupled to vibrating screen 1610. Vibrating screen 1610 gently agitates gelling solution 24 and the objects to be encapsulated or gelled with a force sufficient to prevent two objects within the gelling solution to adhere together. The vibration is, however, gentle enough so as not to break the fragile objects to be encapsulated.

According to an exemplary embodiment, the frequency of vibration for the vibrating screen is from 1 to at least 42 Hz, e.g., for a 2-2.5 in (about 5.1 to about 6.4 cm) hose providing an amplitude of about 5 mm. Preferably, the vibration frequency is from 2 to 30 Hz, or 1 to 20 Hz. Below 2 Hz, for example, at 1 Hz, capsules tend to aggregate. The vibration frequency should not correspond to the anti-resonance frequency of the system, which would not agitate the liquid. The vibration should be applied in such a manner that the liquid is vibrated to provide a sufficient agitation for keeping capsules from gelling together and at the same time not distorting the capsules.

The vibrating tubing in flat coil setup may have a slight slope if the height of the center of the flat coil setup is higher than the outer coils in the flat coil setup.

The vibrating tubing may be completely or partially filled with the continuously flowing liquid gelling solution. If the vibrating tubing is partially filled, the objects to be encapsulated may be vibrated in a controlled manner with a force sufficient to provide controlled residence time and proper agitation. If the vibrated tubing is completely filled, the objects to be encapsulated may still be vibrated in a controlled manner with a force sufficient to provide controlled residence time and proper agitation, although the agitation applied may be higher than for a partially filled tubing.

Figure 18:
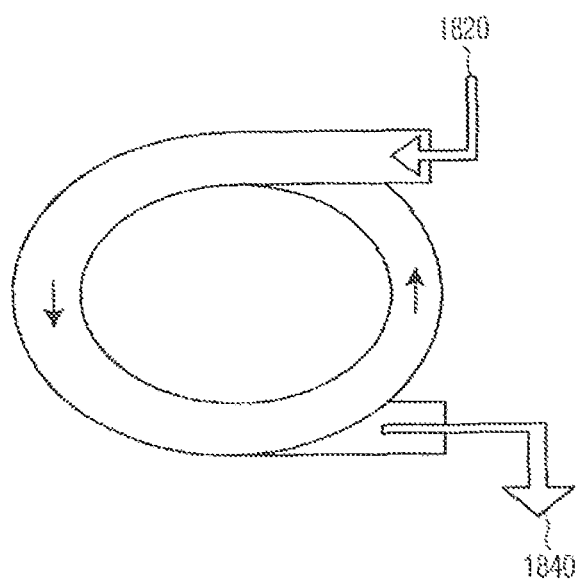
FIG. 18 is a perspective view of a standing spiral, which is another exemplary embodiment of the vibrating tubing.

FIG. 18 is a perspective view of an exemplary standing spiral embodiment of the vibrating tubing according to an aspect of the invention. The standing spiral configuration comprises a length of tubing or other material configured into a series of standing spirals 1810, which are vibrated by means of a vibration device such as a vibrating table. According to this embodiment, the objects to be encapsulated are fed into standing spiral 1810 via input 1820 having a gradual curve 1830. Standing spiral 1810 also contains gelling solution 24. The residence time of objects to be encapsulated or gelled depends on the same parameters as for FIGS. 16 and 17, but there is a contribution from the slope which is given by the diameter of hose/length of one spiral. In example 12, the slope is 5/140. An exemplary linear length of the hose that comprises a standing spiral is from 5-35 meters, for example 20 meters. The average resident time of objects to be encapsulated in the standing spiral range from 20 to 300 sec.

Figure 19:
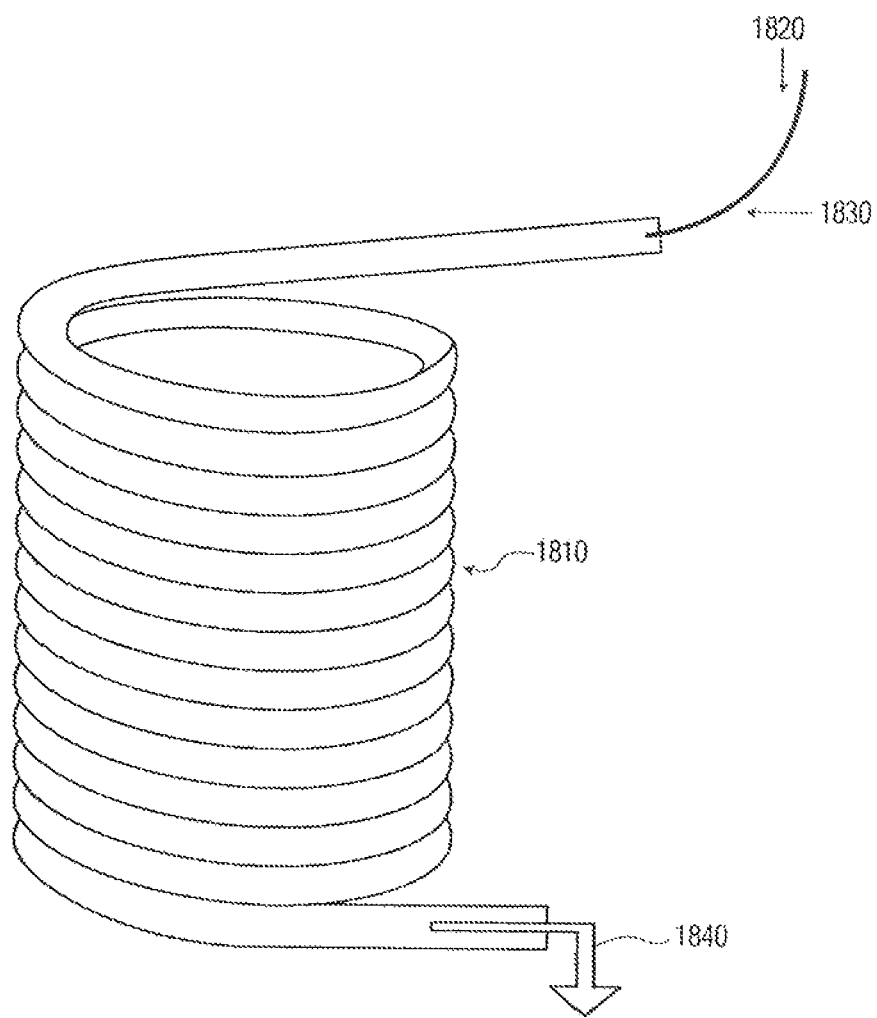
FIG. 19 is a top view of the standing spiral shown in FIG. 18.

FIG. 19 is a top view of the standing spiral of FIG. 18.

Figure 20:
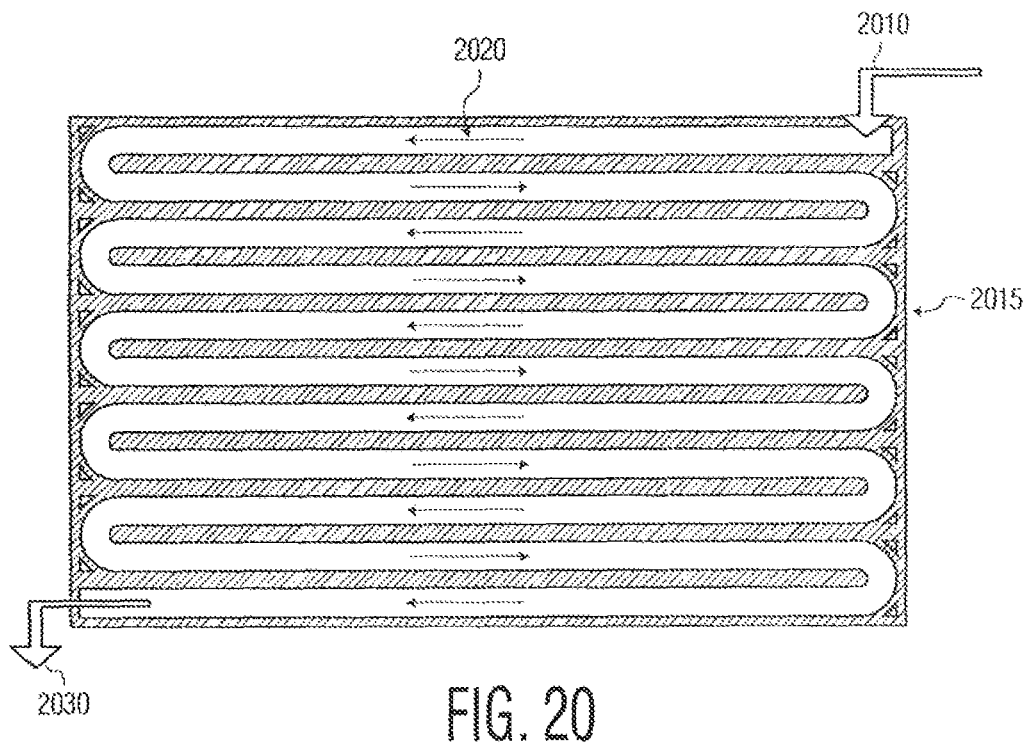
FIG. 20 is a top view of a flume, which is yet another exemplary embodiment of a vibrating tubing.

Gelation of objects may also be performed in a combination of both the flat coil and the standing coil, wherein the combination comprises standing, flat coiled setup FIG. 20 illustrates another embodiment of a vibrating tubing. Shown in FIG. 20 is a top view of a vibrating flume 2000. Vibrating flume 2000 may be vibrated and comprises a series of back and forth channels 2010 filled with gelling solution. According to one embodiment, each successive downstream channel is at the same elevation as the preceding channel, thus being in the same horizontal plane. According to another embodiment, each successive downstream channel is at a slightly lower elevation than the preceding channel. Objects to be encapsulated enter vibrating flume 2000 at input 2015 and exit at 2030. When flume 2000 is vibrated, the objects to be encapsulated flow along the channels in the path and direction as indicated by arrows 2020 in FIG. 20. Vibrating flume 2000 comprises from 1 to 40, 5-25, or 10 channels depending on the channel length. Each channel may be from 2 to 30 ft (about 0.6 to about 9.1 M), 5-20 ft (about 1.5 to about 6.1 M), or 10-15 ft (about 3.0 to about 4.6 M) in length. According to one exemplary embodiment, a series of vibrating flumes 2000 is stacked one on top of the other to provide longer residence times, if needed. In such a setup, the vibrating flumes may be connected through a simple connection such as a pipe or a hose. Alternatively, the vibrating flume may be connected directly if the inlet of the lower flume is situated beneath the outlet of the above flume. This setup with stacked vibrating flumes may advantageously be made with a tubing having a shape of an open U-shaped tube. With this U-shaped tubing, the vibrating flume stacked on top can function as a lid for the flume immediately below it, thus making a closed system that may be easily detached for proper washing and rinsing in cleaning procedures.

FIG. 21 shows flume 2100 manufactured such that initial part 2110 of flume 2100 is particularly steep, with an angle γ between 45° and 90°, preferably between 70° and 90°, and latter part 2120 is less steep, from −10° to 50°, preferably between 0° and 45°. As shown in the drawing, latter part 2120 may comprise more than one section, in which each successive section is less steep than the preceding section. The object to be encapsulated or gelled may be added vertically to the flume at the initial part, thus imparting very low impact with the liquid gelling solution in the flume. The angle between the flume and the addition angle of objects should be kept sufficiently low in order to prevent unwanted deformation of objects at the addition point. The objects travel through flume 2100 to flume exit 2150, where they may be added to the further encapsulation apparatus or vibrating tubing in a controlled manner, such that the impact on the object in the transition between the flume and the further encapsulation apparatus or vibrating tubing may be minimized. The angles on the flume may either be changes in a stepwise fashion, such as in 2 or more bends, or in a continuous fashion, where the angles are varied continuously over the flume length. The liquid gelling solution may be added from flume reservoir 2130, above the initial part of the flume, i.e., through a hose connector at the end wall of the reservoir, or it may added directly to the initial part of the flume. The liquid gelling solution may then resemble a water fall at the initial part of the flume. This flume may be particularly useful for production of larger capsules, which are generally easier to deform upon addition to the gelling bath.

Encapsulation Process

Capsules having a capsule wall of gelled gel-forming polymer are formed by adding portions of an emulsion comprising a suitable gelling agent to an aqueous gelling solution comprising a suitable gel-forming polymer, thereby encapsulating the portions of the emulsion in a layer of gelled gel-forming polymer. The layer of gelled gel-forming polymer, or capsule wall, is formed by gelling the gel-forming polymer with the gelling agent. The gelling agent typically comprises a polyvalent cation, typically a divalent and/or a trivalent cation, or a mixture of polyvalent cations capable of gelling the gel-forming polymer.

The gel-forming polymers are gel-forming polysaccharides, which include, for example, carrageenans, such as kappa, kappa II, and iota carrageenans; alginates; chitosans; and pectins such as low methoxy and amidated low metoxy pectins; and mixtures thereof. A typical concentration of gel-forming polymer in gelling solution 24 is about 0.1 wt % to about 10 wt %, preferably about 0.5 wt % to about 7 wt % by total weight of the gelling solution.

Pectin is a naturally occurring polysaccharide found in the roots, stems, leaves, and fruits of various plants, especially the peel of citrus fruits such as limes, lemons, grapefruits, and oranges. Pectins contain polymeric units derived from D-galacturonic acid. About 20-60% of the units derived from D-galacturonic acid, depending on the source of the pectin, are esterified with methyl groups. These are commercially known as high methoxy pectin and low methoxy pectin, the latter also including amidated pectins.

Carrageenan refers to a group of sulfated galactans extracted from red seaweed. Carrageenans are linear chains of D-galactopyranosyl units joined with alternating (1→3) α-D and (1→4) β-D-glycosidic linkages. Carrageenans may, in part, be distinguished by the degree and position of sulfation. Most sugar units have one or two sulfate groups esterified to a hydroxyl group at carbons C-2 or C-6. There are three main types of carrageenan: kappa carrageenan, iota carrageenan, and lambda carrageenan. Kappa carrageenans produce strong rigid gels while those made with iota carrageenan are flaccid and compliant. Lambda carrageenans do not gel in water. Iota carrageenan has a repeating unit of D-galactose- 4-sulfate-3,6-anhydro-D-galactose-2-sulfate providing a sulfate ester content of about 25 to 34%.

A preferred gel-forming polymer is alginate. Alginates are salts of alginic acid. Alginic acid, which is isolated from seaweed, is a polyuronic acid made up of two uronic acids: D-mannuronic acid (M) and L-guluronic acid (G). Alginates are not random copolymers, but consist of blocks of similar and alternating residues, for example, MMMM, GGGG, and GMGM, and are generally useful in the form of alginic acid or salts thereof. The ratio of mannuronic acid and guluronic acid varies with factors such as seaweed species, plant age, and part of the seaweed (e.g., stem, leaf).

Water insoluble alginate salts, in which the principal cation is calcium, are found in the fronds and stems of seaweeds of the class Phaeophyceae, examples of which are *Fucus vesiculosus, Fucus spiralis, Ascophyllum nodosum, Macrocystis pyrifera, Alaria esculenta, Eclonia maxima, Lessonia nigrescens, Lessonia trabeculata, Laminaria japonica, Durvillea antarctica, Laminaria hyperborea, Laminaria longicruris, Laminaria digitata, Laminaria saccharina, Laminaria cloustoni,* and *Saragassum* sp. Methods for the recovery of alginic acid and its water-soluble salts, especially sodium alginate, from natural sources are well known, and are described, for example, in Green, U.S. Pat. No. 2,036,934, and Le Gloahec, U.S. Pat. No. 2,128,551.

Alginic acid is substantially insoluble in water. It forms water-soluble salts with alkali metals, such as sodium, potassium, and, lithium; magnesium; ammonium; and the substituted ammonium cations derived from lower amines, such as methyl amine, ethanol amine, diethanol amine, dimethylethanol amine, methydiethanol amine, and triethanol amine. These salts are soluble in aqueous media above about pH 4, but are converted to alginic acid when the pH is lowered below about pH 4. A water-insoluble alginate is formed if certain polyvalent cations (gelling agents), especially $Ca^{2+}$, $Ba^{2+}$, $Sr^{2+}$, $Zn^{2+}$, $Fe^{2+}$, $Cu^{2+}$, $Al^{3+}$, and mixtures thereof are present in the medium at appropriate concentrations.

Suitable alginates have a weight-average molecular weight of 20,000 Daltons to 500,000 Daltons and a G-content of at least 30%, preferably about 40% to 80%, or about 50% to 90%. Weight-average molecular weight is calculated by first determining the intrinsic viscosity, then using the Mark-Houwink Sakurada Equation, as in Martinsen, et al; "Comparison of Different Methods for Determination of Molecular Weights and Molecular Weight Distribution of Alginates" (*Carbohydr. Polym.*, 15, 171-193, 1991). A suitable alginate for gelling solution 24 is an alginate having a weight-average molecular weight of 20,000 Daltons to 500,000 Daltons, having a G-content of at least 30%, preferably in the range of 40% to 80%, or 50% to 90%.

A mixture of both low and higher weight-average molecular weight alginates in the gelling solution impart preferable properties to the alginate capsule wall. For example, a preferred mixture of alginates is comprised of (i) an alginate having a low weight-average molecular weight of 30,000 Daltons to 40,000 Daltons, and (ii) an alginate having a higher weight-average molecular weight of 150,000 Daltons to 500,000 Daltons. Increasing the ratio of a higher weight-average molecular weight alginate provides a more elastic alginate gel capsule. Increasing the ratio of the low weight-average molecular weight alginate provides a less viscous gelling solution and a more favorable rate of capsule formation. Depending upon the characteristics desired in the alginate containing capsule wall to be formed around the emulsion, a suitable ratio of low weight-average molecular weight alginate (i) to higher weight-average molecular weight alginate (ii) in the gelling solution is about 0.1 to 20 of (i) to I of (ii) (0.1-20:1), respectively. A preferred ratio of low weight-average molecular weight alginate (i) to higher weight-average molecular weight alginate (ii) is about 1 to 16 of (i) to I of (ii) (1-16:1), respectively.

Gelling solution 24 may contain additional components such as buffers, dyes, secondary film formers, anti-oxidants, plasticizers, stabilizing polymers, emulsion destabilizers, and antifoaming agents. Stabilizing polymers are materials that stabilize the emulsion by increasing the viscosity of the water-phase. Emulsion destabilizers are materials that, when added to the gelling solution, promotes destabilization of the emulsion in the gelling solution. Water typically comprises the balance of the gelling solution.

Water emulsions containing relatively large amounts of oil can be encapsulated by the gel-forming polymers. The oil may comprise at least 50% by total weight of the emulsion. The oil content is calculated based on the total weight of the oil, water, emulsifier and gelling agent in the emulsion. Although, as discussed below, the emulsion can be used as a carrier or vehicle for a variety of added components, the at least 50% by total weight of the emulsion is exclusive of any added components.

The oil is selected from any oil, or combination of oils, that are useful in encapsulated form, for example, for use in the pharmaceutical (pharmaceutical herein includes veterinary and nutraceutical), food, nutritional, cosmetic, agricultural, and the like industries. Suitable oils include, for example, oils derived from animals, plants, microorganisms, or extracts thereof; oils that are chemical compounds derived by synthetic or other means, or formulations thereof; oils that are fatty acids, esters, or derivatives thereof; or oils that may be a pharmaceutically active agent, a nutritional supplement, flavor oil, or a food. Oils also include oils that act as carriers or solvents for oil-soluble active materials such as an oil-soluble pharmaceutically active agent, a nutritional, flavor, fragrance, supplement, or a food. Other oils are those that include naturally occurring emulsifiers. One such oil is soy oil, which contains lecithin. Lecithin is useful in food manufacturing as an emulsifier in products high in fats and oils. Preferred oils are those that are liquid, or that can be made liquid at a temperature of about 20° C. to about 95° C.

An emulsion of oil and water is a heterogeneous system, in which the oil and water are immiscible and either 1) the water is intimately dispersed in the oil, or 2) the oil is intimately dispersed in the water, in which the dispersed material is in the form of droplets. Emulsifying agents, or emulsifiers, are typically used to prevent coalescence of the dispersed phase. An emulsifier typically has 1) a hydrophilic group and 2) a lipophilic group in its structure. As is well known to those skilled in the art, an emulsifier can be characterized by its hydrophilic-lipophilic balance ("HLB"). Useful emulsifiers typically have a HLB value of about 1 to 19. In general, emulsifiers with lower HLB values, for example 3-9, are more suitable for preparing water-in-oil emulsions, and emulsifiers with higher HLB values, for example 9-18, are more suitable for preparing oil-in-water emulsions. However, there are emulsifiers that are useful for both types of emulsions.

Typical emulsifiers include, for example, glycerin fatty acid esters; lactic acid esters of monoglycerides; lecithins; polyglycerol polyricinoleate; sorbitan esters of fatty acids ethoxylates such as polyoxyethylene(20) sorbitan monolaurate (TWEEN® 20), polyoxyethylene sorbitan monopalmitate (TWEEN® 40), polyoxyethylene sorbitan monostearate (TWEEN® 60), polyoxyethylene sorbitan monooleate (TWEEN® 80), and polyoxyethylene sorbitan trioleate (TWEEN® 85); succinic acid esters of monoglycerides; citric acid esters of monoglycerides; diacetyl tartaric acid esters of monoglyceride; polyglycerol esters of fatty acids; sucrose esters of fatty acids; polyoxyethylene sorbitol ester of fatty acids; unsaturated monoglycerides and diglycerides, including monoglycerides and diglycerides of oleic acid, linoleic acid, linolenic acid, or other commonly available higher unsaturated fatty acids; and mixtures thereof. Preferred emulsifiers include, for example, polyoxyethylene (20) sorbitan monolaurate (TWEEN® 20), polyoxyethylene sorbitan monopalmitate (TWEEN® 40), polyglycerol esters of fatty acids, polyglycerol polyricinoleate (PGPR® 90), calcium stearoyl-2-lactylate (VERV® K), sorbitan monooleate (SPAN® 80), and mixtures thereof. More preferred emulsifiers include polyoxyethylene(20) sorbitan monolaurate, polyoxyethylene sorbitan monopalmitate (TWEEN® 40), polyglycerol polyricinoleate, and mixtures thereof.

The emulsion comprises a gelling agent, which gels the gel-forming polymer. Any acid or salt that will gel the gel-forming polymer may be used as the gelling agent. Typically, a salt or combination of salts that provides the desired cation or mixture of cations is used as the gelling agent. The gelling agent comprises a cation, typically a divalent and/or a trivalent cation, or a mixture of cations capable of gelling the gel-forming polymer. Suitable polyvalent cations include, for example, calcium(2+), barium(2+), strontium(2+), iron(2+), zinc(2+), copper(2+), and aluminum(3+). Alternatively, the gel-forming polymer can be gelled by an acid, typically by lowering the pH of the gelling solution to about 4 or below. Preferred cations are divalent metal cations, more preferably the calcium (2+) cation. Preferred gelling agents are water soluble calcium salts, more preferably calcium chloride, in either hydrated or anhydrous form. Alternatively, the gelling agent may be an acid that gels the gel-forming polymer, typically an acid that lowers the pH of the gelling solution to about 4 or below.

Increasing the gelling agent concentration in the emulsion increases the thickness of the capsule wall, thereby making the capsules stronger. The emulsion comprises at least a gel-forming amount of the gelling agent, that is, an amount sufficient to form a capsule wall of gelled gel-forming polymer surrounding object of emulsion. Typically, the gelling agent comprises 25 wt % or less of the emulsion, based on the weight of the emulsion exclusive of any added component or components, preferably from about 2 wt % to about 15 wt % of the emulsion, based on the weight of the emulsion exclusive of any added component or components.

The added optional component may comprise one or more pharmaceutical agents, veterinary agents, nutritional supplements, agricultural agents, foods, cosmetic ingredients, and/or excipients.

Numerous pharmaceutical agents well known to those skilled in the art, for example, cardiovascular-renal drugs; antidiabetic drugs; antidepressants; analgesics; H2 blockers, such as cimetidine and ranitidine; and antibiotics may be used as the added component. Suitable pharmaceutical active agents include, for example, oil-soluble or insoluble drugs, and drugs with a higher water solubility such as paracetamol (acetaminophen), and verapamil hydrochloride. Suitable nutritional supplements include enzymes and co-enzymes such as ubidecarenone (Coenzyme Q10), vitamins, herbs, roots, leafs, fruits, flowers, grasses, barks, fruit peels, and minerals or trace minerals in ionic or elemental form, such as calcium, magnesium, zinc, selenium and iron. Suitable agricultural active agents include herbicides and insecticides. Other suitable components include, for example, dyes; colorants and pigments such as titanium dioxide and calcium carbonate; plasticizers, such as glycerol, sorbitol, mannitol, xylitol, maltitol and polyethylene glycols; preservatives such as lower alkylparabens, benzoic acid, sodium benzoate, and benzyl alcohol, potassium sorbate; and antioxidants such as ascorbic acid and its salts such as sodium ascorbate, sodium D-isoascorbate, ethylenediamine tetraacetic acid (EDTA) salts, ascorbyl palmitate, sulfites, tocopherols, such as a-tocopherol and L-tocopherol, butylated hydroxyanisole and propyl gallate. Other materials that may be encapsulated will be apparent to those skilled in the art. The added component can comprise up to 85% by weight of the dried capsule. Preferably, the added component, when present, comprises 30 wt % to 85 wt % by weight of the dried capsule The added optional component can be added in liquid form, such as simethicone or vitamin E (α-tocopherol) or as solid a solid, such as an insoluble drug. The added component is mixed, prior to or after emulsification of the oil, water, an emulsifier, and gelling agent to form a dispersion. Advantages of adding the components to the emulsion include, for example, the ability to add large amounts of active ingredient just prior to encapsulation and to minimize contact with elevated temperatures, water, and high shear environment, as this can destroy some components by for example decomposition, oxidation and re-crystallization. As a result, the capsules can be pharmaceutical, veterinary, agricultural or nutraceutical solid dosage forms and can be used in specialty applications such as paintballs or as a cosmetic product such as bath oils, etc. Depending on the emulsion used and the components added, the capsules can be manipulated to control the release of the active ingredient as desired in its end use, e.g., in vivo the capsules can be in a form of immediate or delayed release.

The added optional component may comprise one of more plasticizers, antioxidants, preservatives and/or antifoaming agents. Antioxidants are materials that prevent oxidation of the ingredients of the capsule. Preservatives are materials that prevent bacterial growth within the capsule. Antifoaming agents are materials that prevent foaming. Also materials such as cell lines and micro organisms, probiotics, and enzymes may be included in the capsules Plasticizers aid in binding water to the capsule wall of gelled gel-forming polymer, thereby softening of the capsule wall. Plasticizers, such as glycerol, sorbitol, mannitol, xylitol, maltitol and polyethylene glycols, may be added to the gelling bath, the emulsion or in a separate step to soften the capsules. Density adjusters, sometimes known as weighting agents typically are flavorless, oil-soluble materials that have specific gravities greater than those of the oil. They may be added to adjust the density of the emulsion, typically so that it sinks in the gelling solution. Commonly used density adjusters are ester gum, damar gum, and sucrose acetate iso-butyrate (SAIB).

Secondary film formers can be either added to the gelling solution and/or coated onto the capsule wall in a separate step to alter the properties of the capsule wall, for example, the strength, elasticity, gas permeability, solubility, and/or appearance of the capsule wall. Secondary film-formers include, for example, gelling or non-gelling polymers, and enteric polymers for example, alginates, propylene glycol alginate, carrageenans, pectins such as high methoxy (HM), low methoxy (LM), and amidated low methoxy pectins, chitosans, sodium carboxymethylcellulose, carboxymethylcellulose, cellulose acetate phthalate, cellulose acetate succinate, methyl cellulose phthalate, ethylhydroxycellulose phthalate, polyvinylacetatephtalate, polyvinylbutyrate acetate, vinyl acetate-maleic anhydride copolymer, styrene-maleic mono-ester copolymer, methyl acrylate-methacrylic acid copolymer, methacrylate-methacrylic acid-octyl acrylate copolymer and other enteric polymers, cetyl hydroxyethyl cellulose, hydroxypropylmethylcellulose, hydroxypropylcellulose, hydroxyethylcellullose, methylcellulose and other cellulose derivatives, lanolin wax, polyvinyl acetate, polyvinyl pyrrolidone, polyvinyl alcohol, guar gum, acacia gum, pullulan, gellan gum, locust bean gum, xanthan gum, gum tragacanth, starches, maltodextrins, and other secondary gum film-formers. Varying concentrations of secondary film-former provide varying levels of capsule strength and provide varying capsule characteristics, such as release rate.

Sequestrants are compounds that bind or complex the gelling ion, typically calcium, in the capsule wall, thus changing the physical characteristics of the capsule wall, for example, making the capsules more water-soluble. Sequestrants include, for example, sodium citrate, phosphate salts, ethylenediaminetetraacetic acid (EDTA) and salts thereof, and ethylene glycol-bis(p-aminoethyl ester)-N,N,N',N'-tetraacetic acid (EGTA). Washing the capsules with an aqueous solution of alcohol and/or sequestrant can also be used to increase the water solubility of the capsules.

The emulsion may be an oil-in-water emulsion. The emulsion can be prepared by dissolving the gelling agent and at least one emulsifier in water. The resultant mixture may then be homogenized during which time the oil, for example, fish oil, soy oil, oleic acid, or mineral oil, is slowly added to form a highly viscous oil-in-water emulsion. The oil typically comprises about 70% wt % to 98% wt % of the emulsion, based in the weight of the oil, water, emulsifier and gelling agent; preferably, about 85 wt % to 95 wt % by weight of the emulsion, based on the weight of the oil, water, emulsifier and gelling agent.

The emulsion may be a water-in-oil emulsion. The emulsion can be prepared by adding a water solution of the gelling agent and at least one emulsifier to the oil during which time the mixture is homogenized to provide the water-in-oil emulsion. The oil typically comprises about 65 wt % to 85 wt % of the emulsion, based in the weight of the oil, water, emulsifier and gelling agent; preferably, about 70 wt % to 80 wt % by weight of the emulsion, based on the weight of the oil, water, emulsifier and gelling agent. Water-in-oil emulsions of soy oil may be stable for a period of time long enough so that the emulsion can be encapsulated without inclusion of additional emulsifier.

The emulsion may be a water-in-oil-in-water emulsion. A water-in-oil-in-water emulsion provides a means for encapsulating not only an oil, or an oil-soluble substance, but also, a water-soluble substance, or a water-soluble active ingredient. Accordingly, an inner phase comprised of a solution of a water-soluble substance in water can be added to a middle phase comprised of an oil and an emulsifier, for example, polyglycerol polyricinoleate, during which time the mixture can be homogenized to form a water-in-oil emulsion. The so-formed water-in-oil emulsion may then be added to an outer phase comprised of a water solution of gelling agent and emulsifier, for example, polyoxyethylene (20) sorbitan monolaurate (TWEEN® 20), during which time the mixture can be homogenized to form a highly viscous water-in-oil-in-water emulsion. The oil typically comprises about 60 wt % to 90 wt % of the emulsion, based in the weight of the oil, water, emulsifier and gelling agent; preferably, about 70 wt % to 80 wt % by weight of the emulsion, based on the weight of the oil, water, emulsifier and gelling agent. Water-in-oil emulsions of soy oil may be stable for a period of time long enough so that the emulsion can be encapsulated without inclusion of additional emulsifier.

A preferred emulsion is an oil-in-water emulsion. If desired, a drying process at an elevated temperature, for example, at about 60° C., to remove water from the oil-in-water emulsion prior to its encapsulation, can eliminate a large portion of water from the encapsulation step, thereby providing a capsule in a relatively dry form. The length of a separate capsule drying step can therefore be shortened. Additionally, as an aid to shortening the length of a capsule-drying step if one is desired, some of the water in the emulsion can be replaced with a water-miscible solvent, for example a $C_1$-$C_4$ alcohol, such as ethanol.

The methods by which the oil and water emulsions, or dispersions are added to gelling solution 24, inter alia, control the size of the capsules formed. The emulsion, or dispersion, which can be in the form of a thick paste or in the form of a liquid of low viscosity, can be fragmented, or shaped in some manner into portions, either prior to, or simultaneously with, its addition to the gelling solution. Suitable methods for adding the emulsion, or dispersion to the gelling solution include, for example, dropping the emulsion from a pipette, or a nozzle, extruding the emulsion through a chopping mechanism, molding the emulsion in a casting mold, and other methods.

The seamless capsule can be made in a variety of shapes. The shape of the formed capsules can be determined by the method of adding the emulsion or dispersion to the gelling solution and by the specific composition of the emulsion or dispersion. When a low viscosity composition is dropped from a pipette, the end capsules will be spherical. Dropping higher viscosity compositions from a pipette can produce oval capsules. Highly viscous compositions can be molded or extruded. When a mold is used, the mold can be designed to give spherical, oval and oblong capsule shapes. When the composition is extruded through a nozzle and cutting with a cutting device, for example a knife, wire, waterjet, laser or an iris shutter-like device, the shape of the capsules can be determined by the diameter of the hole and length of the cut emulsion fragment. If the diameter of the hole is about the length of the fragment, the capsules can be spherical in shape. If the length of the fragment exceeds the diameter of the hole, the capsules will be oval, oblong or cylindrical in shape. Due to the gelation process, the capsule wall will undergo a certain amount of contraction, whereas sharp edges will be rounded off. The amount of contraction is influenced by the viscosity of the emulsion or the amount of component added to the emulsion vehicle.

The surface of the portions of the emulsion may be reduced in stickiness prior to addition to the gelling solution. A reduction in the stickiness of the surface of the portions of the emulsion may aid in helping to (a) ensure the complete release of the portions from any device used to form, shape (for example, a mold), or transfer the portions to the gelling solution; (b) increase the ease and speed of handling the portions; and/or (c) avoid agglomeration or sticking of the individual portions of the emulsion as they are initially added to the gelling solution. The surface of the portions of the emulsion may be reduced in stickiness by any suitable method that does not interfere with the formation of the polysaccharide gel membrane surrounding the portions of emulsion once they are added to the gelling solution. Such suitable methods to reduce stickiness of the surface of portions of the emulsion include, for example, i) surface-drying, or ii) surface-hardening each portion of the emulsion, or by iii) applying a surface coating to at least part of each portion of the emulsion. Suitable surface coatings, such as release agents, anti-tacking agents and lubricants include, for example, polysaccharides, such as alginates, and other polysaccharides; $C_{10}$-$C_{15}$ alkyl lactates, such as lauryl lactate; calcium silicate, dioctyl malate, magnesium carbonate, D-mannitol, silica, hydrated silica, talc; oils and hydrated oils, such as castor oil, coconut oil, cottonseed oil, palm oil, soybean oil, jojoba oil, apricot oil, kernel oil, mineral oil, olive oil, sesame oil, walnut oil, wheat germ oil, and other oils; waxes, such as lanolin wax, and other waxes; microcrystalline cellulose; stearates, such as isocetyl stearate, isocetyl stearoyl stearate, isopropyl stearate, magnesium stearate, zinc stearate, and other stearates; glycerol derivatives, such as glycerol behenate, glycerol cocoate, glycerol dioleate, glycerol dioleate SE, glycerol distearate, glycerol distearate SE, glycerol laurate SE, glycerol oleate SE, glycerol polymethacrylate, glycerol ricinoleate SE, and other glycerol derivatives; fatty acids, such as palmitic acid, lauric acid, stearic acid, and other fatty acids; polyethyleneglycol (PEG) and derivatives, such as PEG-6, PEG-100, PEG-200, PEG-40 stearate, and other polyethyleneglycol derivatives; combinations thereof, and other surface coatings. More preferably, alginates may be used as the surface coating. In a one method, a portion of the emulsion, or dispersion may be shaped, for example, in a mold, in which at least a part of the mold may be treated with a suitable surface coating, such as an alginate, prior to molding the portion of emulsion, or dispersion thereby imparting a surface coating to at least part of the portion of emulsion, or dispersion. The mold may be treated with an aliquot of the gelling solution 24 or the mold may be treated with different solutions of an alginate.

During the step of encapsulating the oil and water emulsion, or dispersion, it is preferable that the gelling solution be maintained at a temperature of at least 20° C., and, more preferably about 20° C. to about 60° C. Advantageously, the capsule wall will have a higher alginate solids level when performing the encapsulating step at an elevated temperature. In addition, increasing the temperature may increase the rate of gelation and subsequently lower processing times, and also provides capsules with an improved, shiny appearance.

Characteristics desired in the capsule can be optimized during the step of encapsulating by one skilled in the art, depending on the materials used. In general, this step can be accomplished during a period of time up to 240 minutes from the start of the addition of portions of the oil and water emulsion, or dispersion preferably during 2 minutes to 60 minutes, and more preferably, during 10 minutes to 40 minutes. Capsules prepared by the methods set forth above have a capsule diameter of about 1 millimeter to about 40 millimeters, although the diameter of the capsule prepared is not restricted by the method of preparation. The thickness of capsule walls prepared by the methods set forth above is generally about 0.3 millimeter to 4 millimeters.

As discussed the seamless capsules may be of a non-spherical shape, such as oval, oblong or cylindrical in which the capsules have both a length and a diameter where the length differs from the diameter of the capsules, and where either the length or the diameter is about 1 to about 40 mm. Non-spherical, larger capsules, i.e. capsules with a length or a diameter above about 12 mm, may be particularly useful for oral consumption as non-spherical shapes may provide benefits such as ease of swallowing compared to a spherical capsule.

The capsules may be washed or rinsed with an aqueous solution such as water, or an aqueous alcohol solution after the encapsulation step, and prior to the optional plasticizing, drying and coating step. The washed or rinsed capsules might also possibly be transferred to a hardening bath, before they are optionally dried and coated.

The washing step for the capsules may require up to about 4 to about 8 hr of washing to completely remove excess gelling ions from the capsule core. The washing step time depends on formulation and size and shape of the dosage form of the objects to be encapsulated. The washing step may be performed with a 1:1 to 1:8 capsule:water ratio, preferably with a 1:1 to 1:4 ratio. The washing time and ratio may be reduced if washing water is continuously exchanged during the washing time. The temperature at which the washing step occurs ranges from 20 to 100° C., preferably from 20-80° C. Capsules may be gently stirred during the washing step. Washing may be performed with water or an aqueous solution containing additional compounds, such as complexing agents and sequestrants, in order to bind any unreacted gelling ions present in the washing solution as a result of the washing step.

The plasticizing step may be performed after the washing step in order to apply a sufficient amount of plasticizer to the capsules. The plasticizer bath may contain from 0-99% plasticizer, preferably from 7-40%. The plasticizing step can be performed in up to 2 hr, preferably from 2-40 min. The temperature in the plasticizer bath is from 20 to 100° C., preferably from 20-60° C.

Although the drying and coating of the capsules can be done separately and in no special order, one method is to conduct the drying step and coating step simultaneously. The simultaneous drying and coating of the capsules can be accomplished, for example, by 1) subjecting the wet capsules to pre-drying for a short period of time (about 10 minutes) in a fluidized bed apparatus, 2) adding a solution of a coating, then 3) subjecting the coated capsules to another, usually longer drying period, affording the capsules in dry form. A "fluidized bed apparatus" is a device that can be used for drying and/or coating capsules, in which the capsules are placed in a stream of air (the fluid) at a velocity to cause the capsules to float in the stream of air, thereby causing them to dry. One such device is sold under the name and trademark of STREA-1, manufactured by Niro-Aeromatic Ltd, Hauptstrasse 145, CH-4416 Bubendorf, Switzerland.

Depending upon the intended end-use of the capsules, it may be preferable that the capsules be dry. In a drying step, the water that is contained in the now-encapsulated oil and water emulsion and water within the capsule wall is removed. Once "dried", the capsules are considered to be in a "dry form", although one skilled in the art will understand that a capsule in dry form can include some water, for example, up to about 20%. Preferably the water content of the capsules is less than 10% by the total weight of the dried capsules. Once dried, the capsule wall becomes firmer, as it shrinks to form a thinner wall on the outer surface of the capsule. Preferably the contents within the capsule, after drying is present in the amount of at least 70% by weight of the capsule, more preferably at least 90% by weight. Capsules prepared by this method advantageously do not lose their shape upon drying and therefore appear smooth, and seamless. The capsules in dry form may have varying capsule diameters depending on the intended use; e.g., the capsule diameter can be relatively small or somewhat larger, and be about 0.5 millimeter to about 35 millimeters, where the dry polysaccharide gel film generally has a thickness of about 40 μm to 500 μm.

The seamless dry capsules may be of a non-spherical shape, such as oval; oblong; or cylindrical, in which the capsules have both a length and a diameter, the length differs from the diameter of the capsule, and either the length or the diameter is in the range of 0.5 to 35 mm. Non-spherical, larger capsules, i.e. capsules with a length or a diameter above about 12 mm, may be particularly useful for oral consumption as non-spherical shapes may provide benefits such as ease of swallowing compared to a spherical seamless capsule. Typical dimensions for such a large capsule are length of from about 12 mm to about 30 to 35 mm and even 40 mm, for example, from about 15 to about 30-35 mm, from about 18 to about 30-35 mm, from about 20 to about 30-35 mm, or from about 25 to about 30-35 mm, and a diameter of about 5-12 mm, for example, about 7-12 mm, about 8-12 mm, or 10-12 mm. The fill weight for such a large capsule may be about 500-2500 mg, for example, about 750-2000 mg, about 1000-1500 mg, or 1200-1400 mg. The encapsulation apparatus of the invention is suitable for the preparation of these large capsules. During drying, most of the water that formed the encapsulated emulsion is removed, so it is possible to produce large, "oil filled" capsules by the process of encapsulating the emulsion and drying the resulting capsules.

The operation of apparatus is also suitable for encapsulation of objects in which the oil content is lower than 50%. Such objects may, for example be, artificial caviar or fish-eggs in which a controlled residence time and proper agitation is of importance for product attributes. One such method of preparation of artificial fish eggs (artificial caviar) is described in Ueda, U.S. Pat. No. 4,702,921, the disclosure of which is incorporated herein by reference. In this method, the material to be encapsulated typically comprises a water-soluble food coloring agent, such as gardenia color, as well as a water-soluble fish extract, such as salmon and/or anchovy extract, and/or crabmeat extract.

Other objects to be encapsulated may be prepared without liquid oil, thus completely consist of a viscous core, comprising a gelling agent, viscosifier, and a further added component, such as for example pharmaceutical, nutraceutical, food or confectionary component, where the encapsulated objects may be used for example within the pharmaceutical, nutraceutical, food or confectionary area.

Although the operation of the apparatus has been chiefly described with respect to the formation of capsules in which the capsule wall is a layer of gelled gel-forming polymer or gel-forming polysaccharide, its use is not limited to this application. Other uses of the apparatus is described as in the manufacture of conventional polymer beads, where it is surprisingly found that embodiments of the equipment discussed have a huge benefit for continuous production yielding both controlled agitation and controlled residence time with a narrow residence time distribution both for high and low density beads. In the event of making a gelled bead, the liquid gelling solution 24 would comprise the gelling agent, such as $Ca^{2+}$ for alginate, pectin, or iota carrageenan; or $K^+$ for kappa-carrageenan; or where liquid gelling solution 24 is a cold or hot hydrophobic or hydrophilic liquid, such as an oil, in which temperature induced gelation is performed for thermo gelling polymers. Cold-induced gelation may be performed for polymers such as carrageenan, agar-agar or even gelatin, although not preferred due to animals sources, whereas heat-induced gelation may occur for methylcellulose or hydroxypropylemethylcellulose.

In such case the fragments to be gelled comprise the gelling polymer and ingredients to be encapsulated such as cells, bacteria, such as probiotic bacteria, oils, fats, pharmaceuticals, nutraceuticals, confectionary ingredients, such as sugars, flavors or colors, or foods, such as nuts, roots, vegetables, fruits or purees made thereof. The fragments to be gelled may be fragmented by conventional methods such as dropping from a single or multiple nozzles, extrusion through a vibrating nozzle, extrusion through a cutting mechanism, or other conventional methods. As the gelling time can be well controlled with the encapsulation apparatus or vibrating tubing, both partial or complete gelation can be accomplished in a controlled manner. Partial gelation may be observed when only for example the outer part of the gelled bead is gelled. The continuous operation combined with the controlled agitation and residence time of the described equipment may give an advantage for higher production rates, for example with the use of high speed bead formation devices. The described equipment may also be advantageously used combined with conventional vibrational single, dual or multiple nozzle techniques. The liquid gelling solution may be recycled and re-fed into the equipment. The fragment to be gelled may be added through a flume, preferable through a steep flume, into the encapsulation apparatus or vibrating tubing It can be use in numerous encapsulation processes, such as those that involve interfacial polymerization in which one of the reactive intermediates in the object to be encapsulated and the other is in the gelling bath. For example, the object to be encapsulated may be an aliquot of a solution or a fragment of an emulsion that comprises a reactive polyfunctional acid chloride or mixture of polyfunctional acid chlorides and/or a reactive polyfunctional isocyanate or a mixture or reactive polyfunctional isocyanate and/or a reactive polyfunctional sulfonic acid chloride or a mixture of sulfonic acid chlorides, which function as the gelling agent; and the aqueous gelling bath may contain a reactive polyfunctional amine or a mixture of polyfunctional amines, which function as the gel-forming polymer. An interfacial reaction of the isocyanate and/or acid chloride with the amine forms the capsule wall. Encapsulation by interfacial polymerization is well known to those skilled in the art as is disclosed, for example, in Vandegaer, U.S. Pat. No. 3,577,515; DeSavigny, U.S. Pat. No. 3,959,464; Scher, U.S. Pat. No. 4,140,516; Garber, U.S. Pat. No. 4,309,213; and Lim, U.S. Pat. No. 4,324,683, the disclosures of which are all incorporated herein by reference.

Industrial Applicability

The processes and apparatus of the invention can be used to prepare seamless polysaccharide capsules having a high oil content, which can be used to replace gelatin capsules in the delivery of, for example, nutraceuticals or pharmaceuticals, such as fish oils, concentrated omega-3 fatty acids, borage oils, garlic oils, wheat germ oils, flaxseed oil, carrier oils with drugs and other oils currently being delivered in either gelatin capsules or non-animal capsules or enteric coated capsules and pharmaceuticals, when the replacement of gelatin containing capsules is desired for aesthetic, religious, and/or health related reasons.

The advantageous properties of this invention can be observed by reference to the following examples, which illustrate but do not limit the invention.

EXAMPLES

Example 1

This example illustrates the manufacture of oil-containing polysaccharide capsules using an exemplary apparatus of the invention.

An emulsion was made and pumped through a nozzle (8.5 mm diameter). After exiting the nozzle, the emulsion was cut into fragments with a rotating cutting device rotating at 415 rpm comprising two polyamide wires of approximately 0.127 mm in diameter and having a gage thickness weight of 0.7 g added to each wire. The extrusion rate of the emulsion was 955 g/min, yielding 830 fragments of emulsion weighing 1150 mg each minute. These emulsion fragments were added with a 1 meter long feed flume having a slope of ½ to the beach of a drum containing a gelling solution at temperature of about 25° C. The gelling solution comprised alginate and water. The angle of the flume was small and the fragments were fed to the drum into the winding beach from the input end. The stainless winding comprised a drum about 3478 mm in length, with an outer diameter of approximately 1500 mm and wall thickness of 9 mm. The drum housed a 5 mm thick winding containing 20 coils and about a 123 mm pitch. The height the sides of the chamber defined by adjacent coils of the winding was about 200 mm. The rotation of the winding was 1.2 rpm. The capsule had a residence time of 17 min±25 sec. The first chamber of the winding was equipped with a false or declining floor to maintain the height of the gelling solution throughout the drum. The beach had an inner diameter of about 1000 mm, an outer diameter of about 1200 mm and a slope of about ½, and attached to the upper rim of the front plate.

After an average of 17 min in the encapsulation apparatus, the formed capsules were separated from the gelling solution, which were recycled, with a sieve, and transferred to a washing step for 3 hr to remove excess gelling reagents. After washing, the capsules were added to a plasticizing step comprising 10% glycerin for 25 min, before the capsules were retrieved and finally dried. The rejections rates over 10 hr averaged less than 1%.

Example 2

This example illustrates the manufacture of oil-containing polysaccharide capsules using an apparatus of the invention.

An emulsion was made and pumped through a nozzle (9 mm diameter). Just under the nozzle, the emulsion was cut into fragments with a rotating cutting device (500 rpm) comprising two wires, 0.2 mm in diameter. The pump rate was 950 g/min, yielding 1000 fragments of emulsion 950 mg in weight every minute.

These emulsion fragments were added with a 1.2 meter long feed flume having a slope of $\frac{1}{16}$ to a drum containing a gelling solution at temperature of about 36° C. The gelling solution comprised alginate, plasticizer, and water. The angle of the flume was small and the fragments were fed to the drum into the winding from the input end. The stainless winding comprised a 2000.3 mm long drum, with an outer diameter of 1003.3 mm and wall thickness of 4.7 mm. The drum housed a winding containing 20 coils with a 101.6 mm pitch. With a 3.2 mm thickness of the winding, the width of the each chamber formed between adjacent coils was 98.4 mm. The height the sides of the chamber defined by adjacent coils of the winding was about 200 mm. The rotation of the winding was 1 rpm. The capsule had a residence time of 20±½ min. The first chamber of the winding was equipped with a false or declining floor to maintain the height of the gelling solution throughout the drum.

After 20 min in the encapsulation apparatus, the formed capsules were separated from the gelling solution with a sieve, and transferred to a washing step before drying Example 3

In another embodiment, the winding was a regular screw type comprising an axis, and baffles attached to winding. As the winding was rotated and the baffles created sufficient turbulence prevent emulsion fragments in the drum from adhering to each other. The rotating movement also provided a forward motion of each chamber in the winding. The distance between the winding and the plate or drum was sufficiently small in order to both avoid capsules transferring from one segment to the other, and to avoid capsules getting trapped between the winding and the plate or floor of the drum.

The maximum height of liquid and emulsion fragments in one chamber was such that no fragments were transferred to the next chamber. The height of the solution was lower than the axis of the winding. At the output end of the winding, the formed capsules and liquid were discharged, e.g., onto a sieve, and capsules are washed and dried.

Example 4

As another embodiment of the encapsulation apparatus of the invention includes a winding disposed on a perforated plate. The described windings are then placed in an external tank of gelling solution allowing the gelling solution to flow freely through the perforated plate. The liquid height was determined by means of the height of liquid in the external tank. The holes in the perforated plate were much smaller than the gelled product to avoid leakage into the outside tank. The capsules were transferred out of the gelling solution reservoir, when a sufficient positive flow out of the reservoir occurred. Alternatively, the capsules were mechanically transferred out of solution, e.g., with a belt drive or a moving sieve, etc.

Example 5

This example illustrates an exemplary manufacturing process of forming oil-containing polysaccharide capsules using an exemplary flat coil embodiment of the vibrating tubing in combination with an encapsulation device.

An emulsion was made and pumped through a nozzle (9 mm diameter). Just under the nozzle, the emulsion was cut into fragments with a rotating cutting device (500 rpm) comprising two wires, 0.2 mm in diameter. The pump rate was 950 g/min, yielding 1000 fragments of emulsion 950 mg in weight every minute.

These emulsion fragments were added to the flat coil made from a 13 ft (about 4.0 M) long, 2 in (about 5.1 cm) diameter hose configured into a contiguous spiral contained within a 2 ft (about 0.61 M) diameter SWECO® vibrating screen. Residence time in the flat coil was 20±5 sec. The gelling solution disposed in the flat coil comprised alginate and water.

Upon exiting the flat coil, the objects were passed to an encapsulation apparatus. The encapsulation apparatus comprised a drum having a 3478 mm length, with an outer diameter of approximately 1500 mm and wall thickness of 9 mm. The drum housed a 5 mm thick stainless steel winding containing 20 coils and about a 123 mm pitch. The drum also contained a gelling solution maintained at 36° C. The height the sides of a chamber defined by adjacent coils of the winding was about 200 mm. The rotation of the winding was 1.2 rpm. The capsule had a residence time in the encapsulation apparatus of about 18±½ min. The first chamber of the winding was equipped with a false or declining floor to maintain the height of the gelling solution throughout the drum.

The total residence time in both the flat coil and the encapsulation apparatus was 18 min. The formed capsules exiting the encapsulation apparatus were separated from the gelling solution with a sieve, and were subjected to a washing and plasticizing step before drying.

Example 6

This example illustrates an exemplary manufacturing process of an oil-containing polysaccharide capsule formed from an exemplary embodiment of the vibrating tubing in the form of a flat coil, in combination with an encapsulation of the invention.

An emulsion was made and pumped through a nozzle (8.5 mm diameter). Just under the nozzle, the emulsion was cut into fragments with a rotating cutting device (500 rpm) comprising two wires, 0.127 mm in diameter. The pump rate was 1150 g/min, yielding 1000 fragments of emulsion 1150 mg in weight every minute, corresponding to 1000 mg of oil.

These emulsion fragments was collected through a steep (75 degrees) stationary flume, which led to a flat coil comprising a 35 foot (about 10.7 M) long, 2.5 in (about 6.4 cm) diameter hose configured into a spiral and contained within a 4 foot diameter vibrating screen (SWECO® 48 in (about 1.22 M) stainless steel). Residence time in the flat coil was 75±15 sec. The vibration of the SWECO® vibrating screen unit was 11 Hz. The flow of the gelling solution into the flat coil was 12 liters/min. The gelling solution comprised 2.5% alginate and water.

From the flat coil, the emulsion fragments traveled to an encapsulation apparatus. The encapsulation apparatus comprise a drum of about 3478 mm in length, with an outer diameter of approximately 1500 mm and wall thickness of 9 mm. The drum contained a gelling solution at a temperature of about 20° C. The drum housed a 5 mm thick stainless steel winding containing 20 coils and about a 123 mm pitch. The height the sides of the chamber defined by adjacent coils of the winding in the drum was about 200 mm. The rotation of the winding was 1.2 rpm. The residence time of a capsule in the encapsulation apparatus was 17±½ min. The first chamber of the winding of the drum was equipped with a false or declining floor to maintain the height of the gelling solution throughout the drum.

The residence time in both the flat coil and the encapsulation apparatus was about 19 min. The formed capsules exiting the encapsulation apparatus were separated from the gelling solution at the discharge end of the drum, via a lifting discharge mechanism in the form of a shaped sieve attached to the discharge end of the drum. As the drum rotated and the capsule traveled through the last coil of the winding, the capsules were deposited onto the shaped sieve. The shaped sieve then lifted the capsules into a funnel attached to a flume which transported the capsules via gravity into the second encapsulation apparatus.

The second encapsulation apparatus was configured to wash and plasticize the formed capsule. The second encapsulation apparatus comprised a 2000.3 mm long drum, with an outer diameter of 1003.3 mm and wall thickness of 4.7 mm. The drum housed a stainless steel winding containing 20 coils with a 101.6 mm pitch. With a 3.2 mm thickness of the winding, the width of the each chamber formed between adjacent coils was 98.4 mm. The height the sides of the chamber defined by adjacent coils of the winding was about 200 mm. The rotation of the winding was 0.1 rpm. The first 16 coils contained a washing solution and capsules to be washed. The temperature was ambient and the residence time of the objects in the first 16 chambers was 160±5 min. The wall of the drum at the 17$^{th}$ coil was perforated, thereby allowing the washing solution to drain from the drum. At approximately the 17½ coil, the coil was refilled with plasticizer solution containing of 10% glycerin. The last 3 thus contained the plasticizer solution and the capsules had a residence time in the plasticizer solution of about 30±5 min. After the plasticizer treatment, the capsules were discharged from the drum, gently shaken and left for drying in either a tumble drier, tray drier or a combination of both.

The dried capsules had an average length of about 20 mm and a diameter of about 9.4 mm, and had an oblong-like shape. Exemplary capsules formed by Example 6 had less than 0.1% rejected capsules, and no leaking capsules were observed.

Example 7

This example illustrates another embodiment of a manufacturing process for making oil-containing polysaccharide capsules by encapsulation in the vibrating flume embodiment of the vibrating tubing.

An emulsion containing oil, water, emulsifier, color and Ca-salt was manufactured and pumped through a nozzle (7 mm diameter). Just under the nozzle, the emulsion was cut into fragments with a rotating cutting device (367 rpm) comprising one metal wire. The average size of the material to be encapsulated was 500 mg. The hourly production rate was about 22,000 capsules/hr. The run was performed over a time of 19 hr yielding a total of 420,000 capsules.

These emulsion fragments were added to a vibrating flume containing a liquid stream. The stream was flowing through the flume, which was mounted atop a vibrating screen (Carman industries; outer dimensions 140 in (about 356 cm) long, 46 in (about 117 cm) width, 60 in (about 152 cm) height). The flume comprised a series of 10 contiguous channels through which the gelling solution and emulsion fragments flowed. The 10 consecutive channels that comprised the flume each had a length of about 12 ft (about 3.7 M) and connected through bent corners, yielding a total flume linear length of about 120 ft (about 36.6M). The liquid stream contained alginate, glycerin and water. The material to be encapsulated had a residence time in the flume of about 20 min. Upon exiting the flume, the capsules were separated from the liquid by a sieve. The capsules were gently rinsed in water for about 10 sec before they were put for drying. The capsules exhibited an average wall thickness before drying of 800±100 microns. The dry wall thickness after drying was 200±20 microns.

Example 8

This example illustrates an exemplary manufacturing process of making artificial caviar by encapsulation using an exemplary standing spiral embodiment of the vibrating tubing.

An emulsion having a viscosity of 810 cps was formed by emulsification of 300 g of fish oil to 2700 g aqueous phase containing sodium carboxymethyl cellulose (CMC) and calcium chloride dihydrate in water. The emulsion was fragmented into droplets at a rate of 90 droplets/min. The droplets and a gelling solution were added to the standing spiral. The standing spiral was made from a hose having a 2 in (about 5.1 cm) inner diameter. The standing spiral comprised a series of 14 stacked coils of the hose. Each coil had a circumference of about 140 cm, a diameter of about 45 cm, and a slope of ⅟28. The total length of the hose forming the standing spiral was 20 meters. The standing spiral was mounted atop a stirring table (IKA labortechnik KS250) set at 120 rpm (2 Hz) providing vibration to the standing spiral and liquid within. The flow of the liquid was 1.2 liters/min at ambient temperature. Although not added in this example, a water-soluble food coloring agent as well as a water-soluble fish or crabmeat extract could also be added to the emulsion. Droplets and gelling liquid was added through an addition funnel, ensuring droplets being immediately completely covered in liquid. The gelling time in the apparatus was about 3 min. The fish egg resembling capsules was retrieved with a sieve and added to a storing solution. They had a spherical appearance, and no double or triple capsules were observed. The capsules had a diameter of about 4.5 mm and a film thickness of about 0.35 mm.

Example 9

This comparative example illustrates the manufacture of artificial caviar by encapsulation using the apparatus of Example 8, but without the stirring table.

Using the same setup as in Example 8, the vibration of the vibrating table was turned off, and emulsion droplets were added to the flume in a similar manner as in Example 8. It was observed that 10% of the capsules made were either in the form of doubles or triples.

Example 10

This example illustrates an exemplary manufacturing process of forming an oil-containing polysaccharide capsule by encapsulation simulating using multiple standing spirals in series.

An emulsion containing oil, water, emulsifier, color and Ca-salt was manufactured and pumped through a nozzle (8.5 mm diameter). Just under the nozzle, the emulsion was cut into fragments with a rotating cutting device (340 rpm) comprising one metal wire. The average size of the material to be encapsulated was 1150 mg. The fragments and a gelling solution were added to a standing spiral. The standing spiral was made from a hose having a 2 in (about 5.1 cm) inner diameter. The standing spiral comprised a series of 14 stacked spirals of the hose. Each spiral had a circumference of about 140 cm, a diameter of about 45 cm, and a slope of 1/28. The total length of the hose forming the standing spiral was 20 M. The standing spiral was mounted atop a stirring table (IKA labortechnik KS250) set at 180 rpm (3 Hz) providing vibration of the standing spiral and liquid within. The flow of the liquid into the standing spiral was 2.4 liters/min at ambient temperature.

The gelling time in the standing spiral was about 2 min and 10 sec. The wet film thickness was even and calculated to be about 0.45 mm. Some capsules were retrieved from the standing spiral and re-run into the standing spiral an additional 8 times simulating the use of a series of standing spirals. The total residence time of these capsules was of 19.5 min. The film thickness for these capsules was even and measured to be 0.95±0.05 mm. These capsules had an oblong shape were the longer dimension diameter was about 23 mm and the shorter dimension diameter was about 11 mm.

Example 11

This comparative example illustrates the manufacture of oil-containing polysaccharide capsules by encapsulation using the apparatus of Example 10, but without the vibrating table.

Using the same setup as in Example 10, the vibration of the stirring table was turned of, and emulsion fragments were added to the standing spiral in a similar manner. It was observed that capsules were clumping up in the hose, yielding large clusters of sticking fragments. The residence time of the fragments was difficult to calculate due to the clumping, and it was observed that about 97% of the capsules made were rejected.

Example 12

This example illustrates the residence time distribution during capsule formation using a standing spiral embodiment of the vibrating tubing.

Model material (1000 mg alginate capsules) was added to a standing spiral containing a liquid stream in 5 sec intervals. The stream was flowing through the standing spiral made from a hose having a 2 in (about 5.1 cm) inner diameter. The standing spiral comprised a series of 14 stacked spirals. Each spiral had a circumference of about 140 cm, a diameter of about 45 cm, and a slope of 1/28. The total linear length of the hose forming the standing spiral was 20 meters. The standing spiral was mounted atop a stirring table (IKA labortechnik KS250) set at 180 rpm (3 Hz) providing vibration standing spiral and liquid within. The liquid flow into the standing spiral was 2.4 liters/min at ambient temperature. The time at which the model material discharged the standing spiral was recorded and the average residence time was calculated for 20 fragments. The average residence time for these 20 fragments was calculated to be 117.5 sec, with a standard deviation of 1.1 sec. The lowest recorded residence time value was 116 sec and the highest recorded value was 120 sec, suggesting that the residence time distribution for the vibrating liquid setup is narrow.

Example 13

This example illustrates alginate bead formation by encapsulation in a vibrating standing spiral embodiment of the vibrating tubing.

A gel-forming polymer solution containing 2% alginate was added by dripping to the standing spiral containing a liquid stream of gel-inducing liquid comprising 2% calcium chloride dihydrate. The alginate solution was added at a 220 drops/min rate and the Ca-solution flow rate was 0.9 liters/min into the standing spiral. The standing spiral comprised a hose having a 2 in (about 5.1 cm) inner diameter. The standing spiral was wound into 14 coils, each coil having a circumference of about 140 cm, a diameter of about 45 cm, and a slope of 1/28. The total linear length of the standing spiral was 20 meters. The standing spiral was mounted atop a stirring table (IKA labortechnik KS250) set at 150 rpm (2.5 Hz) providing vibration of the standing spiral and liquid therein. The gelling time in the standing spiral was about 105-115 sec.

Example 14

The same apparatus and conditions were used as in Example 13 above, except that the standing spiral was not vibrated. With this configuration, the gelling time for capsule formation was observed to be from about 80-140 sec, a 60 sec variation in gelling time. This range of gelling time was significantly larger than the gelling time when the standing spiral is vibrated as in Example 13.

Example 15

This example illustrates object loaded, sinking alginate bead formation by encapsulation in a vibrating standing spiral embodiment of the vibrating coil.

A gel-forming polymer solution containing 2% alginate and 20% calcium carbonate objects was added dropwise to a vibrating standing spiral having a gel-inducing liquid stream comprising 2% calcium chloride dihydrate flowing at a rate of 0.9 liters/min therethrough. The standing spiral comprised a hose having a 2 in (about 5.1 cm) inner diameter. The standing spiral was wound into 14 coils, each coil having a circumference of about 140 cm, a diameter of about 45 cm, and a slope of 1/28. The total linear length of the standing spiral was 20 M. The standing spiral was mounted atop a stirring table (IKA labortechnik KS250) set at 150 rpm (2.5 Hz) providing vibration of the standing spiral and liquid therein. The average gelling time in the standing spiral was about 140 sec.

Example 16

The same apparatus and conditions were used as in Example 15 above, except that the standing spiral was not vibrated. With this configuration, beads did not exit the standing spiral. Accordingly, with this set-up, vibration of the standing spiral may be necessary for encapsulation of heavy materials.

Example 17

This example illustrates encapsulation of bacteria using alginate bead formation by encapsulation in a vibrating standing spiral.

A gel-forming polymer solution containing 2.4% alginate and 5% *Bifidobacterium bifidum* probiotic bacteria (INTB2, BioCare Ltd, UK) was added drop wise to a vibrating standing spiral containing a liquid, gel-inducing stream comprising 2% calcium chloride dihydrate, flowing into the standing spiral at a rate of 0.9 liters/min. The standing spiral comprised a hose having a 2 in (about 5.1 cm) inner diameter. The standing spiral was wound into 14 coils, each coil having a circumference of about 140 cm, a diameter of about 45 cm, and a slope of 1/28. The total linear length of the standing spiral was 20 M. The standing spiral was mounted atop a stirring table (IKA labortechnik KS250) set at 150 rpm (2.5 Hz) providing vibration of beads and liquid therein. The average gelling time in the standing spiral was about 123±3 sec. The average weight of the beads after gelling and rinsing was 65 mg (n=30).

Example 18

This example illustrates pectin bead formation by encapsulation in a vibrating standing spiral embodiment of the vibrating tubing.

A gel-forming polymer solution containing 4% pectin (LM, amidated), was added dropwise to a vibrating standing spiral containing a liquid, gel-inducing stream comprising 2% calcium chloride dihydrate, flowing into the standing spiral at a rate of 0.9 liters/min. The standing spiral comprised a hose having a 2 in (about 5.1 cm) inner diameter. The standing spiral was wound into 14 coils, each coil having a circumference of about 140 cm, a diameter of about 45 cm, and a slope of 1/28. The total linear length of the standing spiral was 20 M. The standing spiral was mounted atop a stirring table (IKA labortechnik KS250) set at 150 rpm (2.5 Hz) providing vibration of standing spiral and liquid therein. The gelling time in the apparatus was about 120-123 sec.

Having described the invention, we now claim the following and their equivalents.

What is claimed is:

1. A non-spherical seamless capsule comprising oil, wherein the oil is surrounded by a gelled gel-forming polymer comprising alginate, the capsule has a length of 16 mm to 35 mm and a diameter of 5 mm to 12 mm, the capsule is delayed release, and said capsule is made by a process comprising the steps of:
    (a) continuously adding a material to be encapsulated to a tubing containing an aqueous gelling solution comprising a water soluble alginate, the tubing having an input end and an output end, wherein the material is an emulsion comprising oil, water, an emulsifier, and a gelling agent comprising a polyvalent cation and wherein the oil is present in an amount of at least 50% by weight of said emulsion;
    (b) vibrating the tubing to a sufficient degree such that the material passes through the tubing from the input end to the output end in a controlled, agitated manner and with controlled residence time so as to form said seamless capsule;
    (c) washing the capsule for at least three hours in (i) water or (ii) an aqueous solution that does not contain a sequestrant;
    (d) plasticizing the capsule by adding the capsule to a plasticizer bath; and
    (e) drying said capsule.

2. The capsule of claim 1 in which the capsule has a length of 20 mm to 35 mm and a diameter of 7 mm to 12 mm.

3. The capsule of claim 1 in which the capsule has a length of 25 mm to 35 mm and a diameter of 7 mm to 12 mm.

4. The capsule of claim 1 in which the fill weight of the capsule is 500 to 2500 mg.

5. The capsule of claim 1 in which the fill weight of the capsule is 1000 to 1500 mg.

6. The capsule of claim 1 in which the capsule additionally comprises a material selected from the group consisting of pharmaceuticals, nutraceuticals, confectionary ingredients, foods, and mixtures thereof.

7. The capsule of claim 1 in which the water content of the capsules is less than 10% by the total weight of the dried capsules.

8. The capsule of claim 1, wherein said capsule is washed from three to eight hours.

9. The capsule of claim 8, wherein said capsule is washed in water and said capsule to water weight ratio is 1:1-1:8, respectively.

* * * * *